(12) United States Patent
Janulaitis et al.

(10) Patent No.: US 6,867,028 B2
(45) Date of Patent: Mar. 15, 2005

(54) STRAND-SPECIFIC POLYNUCLEOTIDE NICKASES

(75) Inventors: Arvydas Janulaitis, Vilnius (LT);
Komelijus Stankevicius, Vilnius (LT);
Arvydas Lubys, Vilnius (LT);
Algimantas Markauskas, Vilnius (LT)

(73) Assignee: Fermentas AB, Vilnius (LT)

( * ) Notice: Subject to any disclaimer, the term of this patent is extended or adjusted under 35 U.S.C. 154(b) by 0 days.

(21) Appl. No.: 09/883,249

(22) Filed: Jun. 19, 2001

(65) Prior Publication Data

US 2003/0148275 A1 Aug. 7, 2003

(30) Foreign Application Priority Data

Jul. 24, 2000 (GB) ................................ 0018120

(51) Int. Cl.$^7$ .............................. C12N 9/22; C12P 19/34
(52) U.S. Cl. ........................................ 435/194; 435/91.1
(58) Field of Search ................................. 435/199, 91.1, 435/975

(56) References Cited

U.S. PATENT DOCUMENTS

| | | | |
|---|---|---|---|
| 5,928,908 A | 7/1999 | Dunn et al. | |
| 5,968,786 A | 10/1999 | Dunn et al. | |
| 6,191,267 B1 | 2/2001 | Kong et al. | 536/23.4 |
| 6,395,523 B1 * | 5/2002 | Kong et al. | 435/183 |
| 2003/0100094 A1 | 5/2003 | Heiter et al. | 435/199 |

FOREIGN PATENT DOCUMENTS

WO     WO95/09915      4/1995

OTHER PUBLICATIONS

Kuhn, H., et al. (2003) Biochemistry 42, 4985–4992.*
Xu, Y, et al. (2001) Proc. Natl. Acad. Sci., USA 98(23), 12990–12995.*
Abdurashitov et al., "N.BstSE—a site–specific nickase from *Bacillus stearothermophilus*SE–589", Mol Biol (Mosk). Nov.–Dec.1996;30(6);1261–7 (Russian article, English translation enclosed).
Aggarwal, "Structure and function of restriction endonucleases," Curr Opin Struct Biol. Feb. 1995; 5(1):11–9.
Aslanidis et al., "Ligation–independent cloning of PCR products (LIC–PCR)," Nucleic Acids Res. Oct. 25, 1990; 18(20):6069–74.
Bonaldo et al., "Normalization and subtraction: two approaches to facilitate gene discovery," Genome Res. Sep. 1996; 6(9):791–806.
Erskine et al., "Rapid–reaction analysis of plasmid DNA cleavage by the EcoRV restriction endonuclease," Biochemistry. Jun. 17, 1997; 36(24):7567–76.
Geider et al., "Intermediate stages in enzymatic replication of bacteriophage fd duplex DNA," J Biol Chem. Jun. 10, 1982; 257(11):6488–93.

Gruenbaum et al., "Restriction enzyme digestion of hemimethylated DNA," Nucleic Acids Res. 1981; 9(11):2509–15.
Halford et al., "The EcoRI restriction endonuclease, covalently closed DNA and ethidium bromide," Biochem J. 1981; 199(3):767–77.
Meyer et al., "Cleavage site of bacteriophage fd gene II–protein in the origin of viral strand replication," Nature. Mar. 22, 1979; 278:365–7.
Nakamaye et al., "Inhibition of restriction endonuclease Nci I cleavage by phosphorothioate groups and its application to oligonucleotide–directed mutagenesis," Nucleic Acids Res. Dec. 22, 1986; 14(24):9679–98.
Nardone et al., "DNA structural polymorphism modulates the kinetics of superhelical DNA cleavage by BamHI restriction endonuclease," J Biol Chem. Sep. 5, 1990; 265(25):15308–15.
Nobbs et al., "DNA excision by the Sfi I restriction endonuclease," J Mol Biol. Aug. 21, 1998; 281(3):419–32.
Osterlund et al., "Ethidium–bromide–inhibited restriction endonucleases cleave one strand of circular DNA," Gene. Nov. 1982;20(1):121–5.
Peacock et al., "Transformation of *E. coli* using homopolymer–linked plasmid chimeras," Biochim Biophys Acta. Sep. 28, 1981; 655(2):243–50.
Potter et al., "Cleavage of phosphorothioate–substituted DNA by restriction endonucleases," J Biol Chem. Nov. 25, 1984; 259(23):14243–8.
Rashtchian et al., "Uracil DNA glycosylase–mediated cloning of polymerase chain reaction–amplified DNA: application to genomic and cDNA cloning," Anal Biochem. Oct. 1992; 206(1):91–7.
Sayers et al., "Strand specific cleavage of phosphorothioate–containing DNA by reaction with restriction endonucleases in the presence of ethidium bromide," Nucleic Acids Res. Feb. 11, 1988; 16(3):803–14.
Schakowski et al., A novel minimal–size vector (MIDGE) improves transgene expression in colon carcinoma cells and avoids transfection of undesired DNA. Mol Ther. May 2001; 3(5 Pt 1):793–800.
Siksnys et al., "Catalytic and binding properties of restriction endonuclease Cfr9l," Eur J Biochem. Oct. 1, 1993; 217(1):411–9.
Stahl et al., "Introduction of asymmetry in the naturally symmetric restriction endonuclease EcoRV to investigate intersubunit communication in the homodimeric protein," Proc Natl Acad Sci U S A. Jun. 11, 1996; 93(12):6175–80.

(List continued on next page.)

*Primary Examiner*—Charles L. Patterson, Jr.
(74) *Attorney, Agent, or Firm*—Pillsbury Winthrop LLP

(57) ABSTRACT

A strand-specific polynucleotide nickase comprising an endonuclease which comprises a first subunit and a second subunit and which recognises an asymmetric nucleotide recognition sequence, wherein the first subunit comprises a catalytic domain capable of cleaving one strand of a DNA duplex, and the second subunit is incapable of cleaving the other strand of the DNA duplex.

32 Claims, 11 Drawing Sheets

OTHER PUBLICATIONS

Taylor et al., "The rapid generation of oligonucleotide–directed mutations at high frequency using phosphorothioate–modified DNA," Nucleic Acids Res. Dec. 20, 1985; 13(24):8765–85.

Taylor et al., "The use of phosphorothioate–modified DNA in restriction enzyme reactions to prepare nicked DNA," Nucleic Acids Res. Dec. 20, 1985; 13(24):8749–64.

Terry et al., "Mechanism of specific site location and DNA cleavage by EcoR I endonuclease," Gene Amplif Anal. 1987; 5:103–18.

Walker et al., "Isothermal in vitro amplification of DNA by a restriction enzyme/DNA polymerase system," Proc. Natl. Acad. Sci. 1992; 89:392–396.

Xia et al., "A site–specific single strand endonuclease activity induced by NYs–1 virus infection of Chlorella–like green alga," Nucleic Acids Res. Oct. 25, 1988; 16(20):9477–87.

Zebala et al., "Characterization of steady state, single–turnover, and binding kinetics of Taql restriction endonuclease," J Biol Chem. Apr. 25, 1992; 267(12):8097–105.

Zhang et al., "Chlorella virus NY–2A encodes at least 12 DNA endonuclease/methyltransferase genes," Virology. Jan. 20, 1998; 240(2):366–75.

Giraud–Panis, Marie–Josephe et al. "Near–simultaneous DNA cleavage by the subunits of the junction–resolving enzyme T4 endonuclease VII" The EMBO Journal 16:9 (1997) 2528–2534.

Stahl, Frank et al. "Intra– vs Intersubunit Communication in the Homodimeric Restriction Enzyme EcoRV: Thr 37 and Lys 38 Involved in Indirect Readout are Only Important for the Catalytic Activity of their own Subunit" Biochemistry, vol. 37 (1998) 5682–5688.

Stankevicius, Kornelijus et al. "Cloning and Analysis of the Four Genes Coding for Bpu10I Restriction–Modification Enzymes" Nucleic Acids Research 26:4 (1998) 1084–1091.

Janscak, Paul et al. "Single amino acid substitutions in the HsdR subunit of the type IB restriction enzyme EcoAI uncouple the DNA translocation and DNA cleavage activities of the enzyme" Nucleic Acid Research 27:13 (1999) 2638–2643.

Davies, Graham et al. "EcoKI with an amino acid substitution in any one of seven DEAD–box motifs has impaired ATPase and endonuclease activities" Nucleic Acids Research 26:21 (1998) 4828–4836.

Degtyarev, Sergey et al. "II–Q restriction endonucleases—new class of type II enzymes" Nucleic Acids Research 18:19 (1990) 5807–5810.

* cited by examiner

R.Bpu10Iα

| | |
|---|---|
| MGVEQEWIKNITDMYQSPELIPSHASNLLHQLKREKRNEKLKKALEIITP | 50 |
| NYISYISILLNNHNMTRKEIVILVDALNEYMNTLRHPSVKSVFSHQADFY | 100 |
| SSVLPEFFNLLFRNLIKGLNEKIKVNSQKDIIIDCIFDPYNEGRVVFKKK | 150 |
| RVDVAIILKNKFVFNNVEISDFAIPLVAIEIKTNLDKNMLSGIEQSVDSL | 200 |
| KETFPLCLYYCITELADFAIEKQNYASTHIDEVFILRKQKRGPVRRGTPL | 250 |
| EVVHADLILEVVEQVGEHLSKFKDPIKTLKARMTEGYLIKGKGK | 294 |

R.Bpu10Iβ

| | |
|---|---|
| MTQIDLSNTKHGSILFEKQKNVKEKYLQQAYKHYLYFRRSIDGLEITNDE | 50 |
| AIFKLTQAANNYRDNVLYLFESRPNSGQEAFRYTILEEFFYHLFKDLVKK | 100 |
| KFNQEPSSIVMGKANSYVSLSFSPESFLGLYENPIPYIHTKDQDFVLGCA | 150 |
| VDLKISPKNELNKENETEIVVPVIAIECKTYIERNMLDSCAATASRLKAA | 200 |
| MPYCLYIVASEYMKMDQAYPELTDIDEVFILCKASVGERTALKKKGLPPH | 250 |
| KLDENLMVELFHMVRRHLNRVWWSPNEALSRGRVIGRP | 288 |

FIGURE 1

| Subunit | Mutation* | Cleavage of dsDNA | Nicking activity |
|---|---|---|---|
| Bpu10I α | D171A | +++ | - |
| Bpu10I α | E180A | ++ | + |
| Bpu10I α | E180Q | + | ++ |
| Bpu10I β | E168A | +++ | - |
| Bpu10I β | E177A | - | +++ |
| Bpu10I β | E177Q | + | +++ |
| Bpu10I β | K179 | - | - |

FIGURE 2

SEQUENCE LISTING

<160> NUMBER OF SEQ ID NOS: 18

<210> SEQ ID NO 1
<211> LENGTH: 294
<212> TYPE: PRT
<213> ORGANISM: Bacillus pumilus

<400> SEQUENCE: 1

Met Gly Val Glu Gln Glu Trp Ile Lys Asn Ile Thr Asp Met Tyr Gln
 1               5                  10                  15

Ser Pro Glu Leu Ile Pro Ser His Ala Ser Asn Leu Leu His Gln Leu
            20                  25                  30

Lys Arg Glu Lys Arg Asn Glu Lys Leu Lys Lys Ala Leu Glu Ile Ile
        35                  40                  45

Thr Pro Asn Tyr Ile Ser Tyr Ile Ser Ile Leu Leu Asn Asn His Asn
    50                  55                  60

Met Thr Arg Lys Glu Ile Val Ile Leu Val Asp Ala Leu Asn Glu Tyr
65                  70                  75                  80

Met Asn Thr Leu Arg His Pro Ser Val Lys Ser Val Phe Ser His Gln
                85                  90                  95

Ala Asp Phe Tyr Ser Ser Val Leu Pro Glu Phe Phe Asn Leu Leu Phe
           100                 105                 110

Arg Asn Leu Ile Lys Gly Leu Asn Glu Lys Ile Lys Val Asn Ser Gln
        115                 120                 125

Lys Asp Ile Ile Ile Asp Cys Ile Phe Asp Pro Tyr Asn Glu Gly Arg
    130                 135                 140

Val Val Phe Lys Lys Arg Val Asp Val Ala Ile Ile Leu Lys Asn
145                 150                 155                 160

Lys Phe Val Phe Asn Asn Val Glu Ile Ser Asp Phe Ala Ile Pro Leu
                165                 170                 175

Val Ala Ile Glu Ile Lys Thr Asn Leu Asp Lys Asn Met Leu Ser Gly
            180                 185                 190

Ile Glu Gln Ser Val Asp Ser Leu Lys Glu Thr Phe Pro Leu Cys Leu
        195                 200                 205

Tyr Tyr Cys Ile Thr Glu Leu Ala Asp Phe Ala Ile Glu Lys Gln Asn
    210                 215                 220

Tyr Ala Ser Thr His Ile Asp Glu Val Phe Ile Leu Arg Lys Gln Lys
225                 230                 235                 240

Arg Gly Pro Val Arg Arg Gly Thr Pro Leu Glu Val Val His Ala Asp
                245                 250                 255

Leu Ile Leu Glu Val Val Glu Gln Val Gly Glu His Leu Ser Lys Phe
            260                 265                 270

Lys Asp Pro Ile Lys Thr Leu Lys Ala Arg Met Thr Glu Gly Tyr Leu
        275                 280                 285

Ile Lys Gly Lys Gly Lys
    290

<210> SEQ ID NO 2
<211> LENGTH: 288
<212> TYPE: PRT
<213> ORGANISM: Bacillus pumilus

<400> SEQUENCE: 2

Met Thr Gln Ile Asp Leu Ser Asn Thr Lys His Gly Ser Ile Leu Phe
 1               5                  10                  15

-continued

Glu Lys Gln Lys Asn Val Lys Glu Lys Tyr Leu Gln Gln Ala Tyr Lys
            20                  25                  30

His Tyr Leu Tyr Phe Arg Arg Ser Ile Asp Gly Leu Glu Ile Thr Asn
        35                  40                  45

Asp Glu Ala Ile Phe Lys Leu Thr Gln Ala Ala Asn Asn Tyr Arg Asp
    50                  55                  60

Asn Val Leu Tyr Leu Phe Glu Ser Arg Pro Asn Ser Gly Gln Glu Ala
65                  70                  75                  80

Phe Arg Tyr Thr Ile Leu Glu Glu Phe Phe Tyr His Leu Phe Lys Asp
            85                  90                  95

Leu Val Lys Lys Lys Phe Asn Gln Glu Pro Ser Ser Ile Val Met Gly
            100                 105                 110

Lys Ala Asn Ser Tyr Val Ser Leu Ser Phe Ser Pro Glu Ser Phe Leu
        115                 120                 125

Gly Leu Tyr Glu Asn Pro Ile Pro Tyr Ile His Thr Lys Asp Gln Asp
130                 135                 140

Phe Val Leu Gly Cys Ala Val Asp Leu Lys Ile Ser Pro Lys Asn Glu
145                 150                 155                 160

Leu Asn Lys Glu Asn Glu Thr Glu Ile Val Val Pro Val Ile Ala Ile
            165                 170                 175

Glu Cys Lys Thr Tyr Ile Glu Arg Asn Met Leu Asp Ser Cys Ala Ala
            180                 185                 190

Thr Ala Ser Arg Leu Lys Ala Ala Met Pro Tyr Cys Leu Tyr Ile Val
            195                 200                 205

Ala Ser Glu Tyr Met Lys Met Asp Gln Ala Tyr Pro Glu Leu Thr Asp
    210                 215                 220

Ile Asp Glu Val Phe Ile Leu Cys Lys Ala Ser Val Gly Glu Arg Thr
225                 230                 235                 240

Ala Leu Lys Lys Lys Gly Leu Pro Pro His Lys Leu Asp Glu Asn Leu
            245                 250                 255

Met Val Glu Leu Phe His Met Val Glu Arg His Leu Asn Arg Val Trp
            260                 265                 270

Trp Ser Pro Asn Glu Ala Leu Ser Arg Gly Arg Val Ile Gly Arg Pro
            275                 280                 285

```
<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: a, t, c or g
<220> FEATURE:
<221> NAME/KEY: modified_base
<222> LOCATION: (8)..(10)
<223> OTHER INFORMATION: a, t, c or g

<400> SEQUENCE: 3 cctnagcnnn                                                          10

<210> SEQ ID NO 4
<211> LENGTH: 12
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, t, c or g
<220> FEATURE:
<221> NAME/KEY: modified_base
<222> LOCATION: (10)..(12)
<223> OTHER INFORMATION: a, t, c or g

<400> SEQUENCE: 4
nnnctgcagn nn                                                               12

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, t, c or g
<220> FEATURE:
<221> NAME/KEY: modified_base
<222> LOCATION: (7)
<223> OTHER INFORMATION: a, t, c or g

<400> SEQUENCE: 5 nnngctnagg                                                                  10

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, t, c or g
<220> FEATURE:
<221> NAME/KEY: modified_base
<222> LOCATION: (25)..(29)
<223> OTHER INFORMATION: a, t, c or g
<220> FEATURE:
<221> NAME/KEY: modified_base
<222> LOCATION: (52)..(53)
<223> OTHER INFORMATION: a, t, c or g

<400> SEQUENCE: 6
nngcttagga gttttctcct aagcnnnnng cttaaggtca agacctaag cnn                   53

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(16)
<223> OTHER INFORMATION: a, t, c or g

<400> SEQUENCE: 7
ttctcctaag cnnnnngctt aggtctt                                               27
```

```
<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(16)
<223> OTHER INFORMATION: a, t, c or g

<400> SEQUENCE: 8
ttgacctaag cnnnnngctt aggagtt                                          27

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved motif
<220> FEATURE:
<221> NAME/KEY: MOD_RES
<222> LOCATION: (1)
<223> OTHER INFORMATION: Glu or Asp
<220> FEATURE:
<221> NAME/KEY: MOD_RES
<222> LOCATION: (2)..(16)
<223> OTHER INFORMATION: Variable amino acid; this region may
      encompass 9-15 residues according to the specification as filed
<220> FEATURE:
<221> NAME/KEY: MOD_RES
<222> LOCATION: (18)
<223> OTHER INFORMATION: Variable amino acid

<400> SEQUENCE: 9

Xaa Xaa Xaa Xaa Xaa Xaa Xaa Xaa Xaa Xaa Xaa Xaa Xaa Xaa Xaa Xaa
 1               5                  10                  15

Glu Xaa Lys

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved motif
<220> FEATURE:
<221> NAME/KEY: MOD_RES
<222> LOCATION: (3)..(10)
<223> OTHER INFORMATION: Variable amino acid
<220> FEATURE:
<221> NAME/KEY: MOD_RES
<222> LOCATION: (12)
<223> OTHER INFORMATION: Variable amino acid

<400> SEQUENCE: 10

Ser Asp Xaa Xaa Xaa Xaa Xaa Xaa Xaa Xaa Glu Xaa Lys
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved motif
<220> FEATURE:
<221> NAME/KEY: MOD_RES
<222> LOCATION: (3)..(10)
<223> OTHER INFORMATION: Variable amino acid
```

```
<220> FEATURE:
<221> NAME/KEY: MOD_RES
<222> LOCATION: (12)
<223> OTHER INFORMATION: Variable amino acid

<400> SEQUENCE: 11

Thr Glu Xaa Xaa Xaa Xaa Xaa Xaa Xaa Xaa Glu Xaa Lys
 1               5                   10

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
tggttatatt gaccatgc                                                  18

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
ttaaaatagt tgttatagat a                                              21

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oliognucleotide

<400> SEQUENCE: 14
cctaagctca ctctcaatgg tctgcagagg tcagacacgc ttaggcatg                49

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      oliognucleotide

<400> SEQUENCE: 15
cctaagcgtg tctgacctct gcagaccatt gagagtgagc ttagggtac                49

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Primer
<220> FEATURE:
<223> OTHER INFORMATION: Description of Artificial Sequence: Primer

<400> SEQUENCE: 16
cgugucugac cugaaaaaat a                                              21

<210> SEQ ID NO 17
<211> LENGTH: 21
<212> TYPE: DNA
```

-continued

```
<213> ORGANISM: Artificial Sequence
<220> FEATURE:
<223> OTHER INFORMATION: Description of Combined DNA/RNA Molecule:
      Primer
<220> FEATURE:
<223> OTHER INFORMATION: Description of Artificial Sequence: Primer

<400> SEQUENCE: 17
gcucacucuc aauggtggcg g                                              21

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:
      Illustrative conserved motif
<220> FEATURE:
<221> NAME/KEY: MOD_RES
<222> LOCATION: (1)
<223> OTHER INFORMATION: Glu or Asp
<220> FEATURE:
<221> NAME/KEY: MOD_RES
<222> LOCATION: (2)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid

<400> SEQUENCE: 18

Xaa Xaa Xaa Xaa Xaa Xaa Xaa Xaa Xaa Glu Xaa Lys
 1               5                  10
```

STRAND-SPECIFIC POLYNUCLEOTIDE NICKASES

The present invention relates to nucleases, especially strand-specific polynucleotide nickases, and to processes for producing such nickases. The invention also relates to certain uses of, and to kits comprising such nickases.

Nickases are endonucleases which cleave only a single strand of a DNA duplex. Some nickases introduce single-stranded nicks only at particular sites on a DNA molecule, by binding to and recognising a particular nucleotide recognition sequence. A number of naturally-occurring nickases have been discovered, of which at present the sequence recognition properties have been determined for four. Two of them recognize degenerate trinucleotides: R/AG—N.CviQXI (18) and C/CD—N.CviPII (19). The third and the fourth isoschizomeric enzymes—N.BstSEI and N.BstNBI, isolated from *Bacillus stearothermophilus* recognize the pentanucleotide GAGTC(N)4/ and nick outside the sequence (20). An enzyme which was capable of introducing single-stranded nicks into double-stranded DNA might find wide application in a number of methods in molecular biology. However the practical application of all identified naturally-occurring nickases is very limited or almost impossible in the majority of methods, because their short recognition sequences result in too frequent cleavage.

During studies of replication initiation mechanisms specific nickases have been discovered as well. One of the best-studied examples is bacteriophage fd gene II protein (gpII protein), which nicks one DNA strand in the phage origin of replication and initiates the replication process (21, 22). Unlike in other known cases, no intermediary covalent protein complex with the 5' end of the nicked strand is formed during DNA hydrolysis, and so there is a possibility to use this protein in some applications. The application of gpII protein in the preparation of single stranded DNA is described in International patent application WO9509915A1. The DNA fragment to be mutagenized is cloned into a special vector containing fd phage origin of replication sequence. Obtained supercoiled circular plasmid DNA is treated with protein gp2 that introduces a nick into one DNA strand. The nicked DNA strand is further degraded with *E. coli* ExoIII, and in this way the obtained single stranded circular DNA may be used either for annealing with the mutagenic synthetic primer (23), for site specific mutagenesis or for differential display (24). U.S. Pat. Nos. 5,968,786 and 5,928,908 describe the applications of gpII protein for the production of labelled single stranded DNA probes and for introducing unidirectional nested deletions.

The major imperfection of this protein is that nicking of DNA is not very efficient so it is impossible to achieve nicking of all substrate. A typical yield is only 50–60 percent. This is quite inconvenient since it causes high background and in order to decrease the background additional purification of nicked DNA from the non-nicked form is necessary. The other inconvenience is that this protein can introduce a nick into only one DNA strand. If the other DNA strand is to be nicked, the DNA fragment has to be subcloned into another vector containing fd origin in the opposite orientation. In this case additional manipulations taking a few days are necessary.

A sequence-specific nickase has been produced by modifying the type II restriction endonuclease EcoRV (17). However this mutant nickase has no specificity regarding DNA strand and therefore the practical application of such a mutant is very limited.

EcoR1 is a type II restriction endonuclease which cleaves both strands of double-stranded DNA within a particular recognition sequence. S. E. Halford and N. P. Johnson showed that the addition of ethidium bromide (EtBr) during cleavage of supercoiled plasmid with EcoRI does not influence the rate of formation of the nicked circular plasmid form (the first stage of reaction), but significantly inhibits the formation of the linear DNA form (the second stage) (7). So the addition of EtBr into the reaction buffer converts EcoRI into a specific nickase. The same phenomenon has been demonstrated for several other restriction endonucleases: HindIII, BglI, PstI, HincII and PvuII (8). However, it was shown that even though DNA molecules with single-strand breaks were the major reaction product, at the same time a significant portion of the substrate was either completely uncleaved or both DNA strands were hydrolysed (8). The other problem significantly limiting the application of this effect for practical purposes is that although type II restriction endonucleases maintain strict specificity for nucleotide sequence, they have no specificity for a particular DNA strand, i.e. + and − strands are nicked with the same efficiency.

Due to the disadvantages of the above methods, attempts to introduce strand-specific nicks into double-stranded DNA have focused on protecting a single strand from cleavage by a restriction endonuclease by modification of the DNA molecule itself. Studies on cleavage of hemimethylated DNA by restriction endonucleases revealed that some enzymes, e.g. MspI and HaeIII cleave only the non-methylated DNA strand in hemimethylated sequences (9). In this case strand-specific nicking of DNA is achieved. The main limitation of this method is that the majority of restriction endonucleases do not cleave hemimethylated substrates at all or cleave both DNA strands, so this procedure is not widely applied (9). Furthermore, the strand to be protected from cleavage must be selectively methylated prior to the nicking reaction.

Another way to obtain strand-specific nicks in DNA was found while studying cleavage of phosphorothioate-substituted DNA by restriction endonucleases (10, 11, 12). When the phosphate group of the phosphodiester bond was substituted by thiophosphate in one DNA strand, some restriction endonucleases hydrolysed only the non-modified strand. Some restriction enzymes are insensitive to such DNA modification and hydrolyse quite effectively both DNA strands unless and until EtBr is added into the reaction mixture (13). After addition of EtBr into the reaction mixture, specific and selective cleavage of the non-modified DNA strand is achieved.

These methods of DNA nicking by restriction enzymes involving modification of one DNA strand were applied to site-specific mutagenesis (14, 15) and later to isothermal DNA amplification (16). However, the methods described are not applicable to native DNA and require either enzymatic manipulations in vitro, or in the case of isothermal DNA amplification, the use of chemically modified synthetic primers prior to the nicking reaction.

The present invention aims to overcome the disadvantages associated with the enzymes and methods of the prior art. In particular the present invention aims to provide a nickase capable of cleaving a pre-selected DNA strand.

Accordingly, the present invention provides a strand-specific polynucleotide nickase comprising an endonuclease which comprises a first subunit and a second subunit and which recognises an asymmetric nucleotide recognition sequence, wherein the first subunit comprises a catalytic domain capable of cleaving one strand of a DNA duplex, and the second subunit is incapable of cleaving the other strand of the DNA duplex.

The nickases of the present invention are advantageous over the prior art, because they are capable of nicking a pre-selected DNA strand at a sequence-specific site. Furthermore a pair of nickases recognising the same asymmetric recognition sequence but nicking different DNA strands provides a simple system that enables either strand to be selected for nicking at a particular site. Additional DNA manipulations are unnecessary, so that there is no need for complementary DNA strand synthesis using dNTP analogues (as in the case of methods employing hemimethylated or phosphorothioate-substituted DNA) or DNA subcloning into another vector as is the case when gpII protein is used.

By "strand-specific" in relation to the nickases of the present invention, it is meant that when the recognition sequence is present the nickases are capable of cleaving a particular strand of a DNA duplex, which strand may be determined by the orientation of the recognition sequence. The nickases recognise an asymmetric recognition sequence, which means that in the recognition sequence one strand of the DNA duplex does not possess the same sequence as the complementary strand, when each strand is read in the 5' to 3' direction. The particular strand which will be cleaved by the nickase may therefore be determined if the sequence is known.

The length of the recognition sequence is not particularly limited, provided that it is long enough so that the number of occurences of the recognition sequence in a particular DNA molecule which is to be treated with the nickase is not too high. In a number of applications of the present nickases it may be desirable to introduce only a single nick into the DNA molecule at a known site. If the recognition sequence is too short, the probability of introducing additional undesired nicks into the DNA will be increased. The length of the recognition sequence may however be lower if the nickase is to be used with shorter DNA molecules. Preferably the recognition sequence comprises 4 or more nucleotides, more preferably 5 or more nucleotides, and most preferably 6 or more nucleotides.

The nickases according to the present invention comprise an endonuclease which comprises a first subunit and a second subunit, where the first subunit comprises a catalytic domain capable of cleaving one strand of the DNA duplex. The nature of the first subunit is not particularly limited, provided that it contains a catalytic domain with the above activity, and that a nickase comprising this subunit recognises an asymmetric sequence. In a preferred embodiment the first subunit comprises a subunit from a type II restriction endonuclease. Preferably the first subunit comprises a subunit from a heteromeric restriction endonuclease. More preferably the first subunit comprises a subunit from the restriction endonuclease R.Bpu10I, an enzyme prepared from *Bacillus pumilus* 10 (see reference 25).

The catalytic domain of the first subunit may cleave one strand of the DNA duplex at any particular site, upstream or downstream of the recognition sequence or within the recognition sequence. Preferably the catalytic domain is capable of cleaving one strand of the DNA duplex within the recognition sequence. This is because when the cleavage site is within the recognition sequence, the sequence immediately either side of the cleavage site may be determined, even if the remaining sequence of the DNA molecule is unknown. This may be useful in subsequent applications of the nicked DNA molecule.

The nature of the second subunit is not particularly limited, provided that it is incapable of cleaving the other strand of the DNA duplex and that a nickase comprising this subunit shows the properties of DNA recognition and cleavage mentioned above. Preferably the second subunit comprises an inactivated endonuclease catalytic domain. The catalytic domain may be inactivated by any known method, preferably by site-specific or non-specific mutagenesis of the subunit. Preferably the second subunit comprises a modified subunit from a type II restriction endonuclease. More preferably the second subunit comprises a subunit from a heteromeric restriction endonuclease modified to render inactive the catalytic domain thereof. Most preferably the second subunit comprises an inactivated subunit from R.Bpu10I.

Without being bound by theory, it is believed that the second subunit may act to stabilise the first subunit and/or to promote the catalytic activity of the first subunit. The second subunit may also be necessary for sequence recognition by the nickase. In a preferred embodiment, the catalytic domain of the first subunit is incapable of cleaving one strand of the DNA duplex in the absence of the second subunit. This is because the presence of the second subunit may ensure that the first subunit shows the correct sequence recognition and cleavage properties.

The first subunit and the second subunit may comprise subunits from different restriction endonucleases, provided that when they are combined in an endonuclease, the endonuclease shows the appropriate sequence recognition properties and cleaves a single strand of the DNA duplex. Preferably the first subunit and the second subunit comprise a non-modified and a modified subunit from the same restriction endonuclease, more preferably from the same heteromeric restriction endonuclease. It is preferable to combine subunits from the same restriction endonuclease in the nickases of the present invention, because provided the second subunit is modified in such a way only as to inactivate its catalytic domain, it is likely that the second subunit will support the sequence recognition and cleavage properties of the first subunit.

Subunits from heteromeric restriction endonucleases are particularly suited for use as subunits for the nickases of the present invention. Because a heteromeric restriction endonuclease comprises at least two distinct subunits, each of these subunits may be responsible for cleavage of a particular DNA strand. For example a heteromeric restriction endonuclease may comprise a subunit which cleaves a DNA strand which may be designated the (+) strand, and a subunit which cleaves a DNA strand which may be designated the (−) strand. Provided that the endonuclease recognises an asymmetric nucleotide recognition sequence, combining the subunit which cleaves the (−) strand comprising an inactivated catalytic domain with an unmodified subunit from the same endonuclease which cleaves the (+) strand may provide a nickase capable of cleaving only the (+) strand. A nickase capable of cleaving the (−) DNA strand may be provided by modifying the subunit which cleaves the (+) strand, and combining this modified subunit with an unmodified subunit capable of cleaving the (−) DNA strand.

In a further aspect the present invention provides a process for producing a strand-specific polynucleotide nickase, which process comprises inactivating the catalytic activity of one subunit of a restriction endonuclease, wherein the endonuclease comprises a first subunit comprising a catalytic domain capable of cleaving one strand of a DNA duplex and a second subunit comprising a catalytic domain capable of cleaving the other strand of the DNA duplex, and the endonuclease recognises an asymmetric nucleotide recognition sequence. This process is particularly suited to producing certain nickases according to the present invention. The invention also provides a strand-specific polynucleotide nickase obtainable by a such a process.

By "inactivating the catalytic activity of one subunit of a restriction endonuclease" it is meant that one subunit of the endonuclease is modified such that the endonuclease is no longer capable of cleaving both strands of the DNA duplex, but remains capable of cleaving a single strand. The method used to inactivate the catalytic activity of one subunit is not especially limited, provided that the other subunit retains some catalytic activity and that the endonuclease is still capable of recognising the recognition sequence. Preferably the catalytic activity of one subunit is inactivated without substantially affecting the catalytic activity of the other subunit or the sequence recognition properties of the endonuclease. Preferably the protein interactions between subunits are substantially preserved.

In a preferred embodiment the step of inactivating the catalytic activity of one subunit comprises non-specific mutagenesis of the subunit. In this procedure mutations are introduced randomly at various locations throughout the subunit. Mutants incorporating mutations at different positions are then assayed for sequence recognition and DNA cleavage activity.

In another preferred embodiment, the step of inactivating the catalytic activity of one subunit of the restriction endonuclease comprises identifying the catalytic domain of the subunit and subsequently introducing mutations into the catalytic domain by site-specific mutagenesis. In this embodiment the catalytic domain may be identified by any suitable method, preferably by comparing the protein sequence of the subunit with the protein sequence motifs from other restriction endonucleases. By "protein sequence motifs" it is meant in particular the sequences of the known catalytic domains of other restriction endonucleases, such as the $(E/D)X_{9-15}EXK$ (SEQ ID NO: 9) motif characteristic of some endonucleases.

The length of the recognition sequence of the endonuclease in the above process is not particularly limited, provided that it is of a suitable length for the nickase which is to be produced. Preferably the recognition sequence comprises 4 or more nucleotides, more preferably 5 or more nucleotides, and most preferably 6 or more nucleotides.

The endonuclease of the above process may cleave both strands of the DNA duplex at any particular sites, upstream or downstream of the recognition sequence or within the recognition sequence. Preferably the endonuclease is capable of cleaving at least one strand of the DNA duplex within the recognition sequence. More preferably the endonuclease is capable of cleaving both strands of the DNA duplex within the recognition sequence.

The other properties of the endonuclease of the present process are not particularly limited, provided that the endonuclease shows the DNA cleavage and sequence recognition properties mentioned above. In a preferred embodiment the endonuclease comprises a type II restriction endonuclease. The endonuclease may comprise two or more identical subunits, or may comprise two or more non-identical subunits. Preferably the endonuclease comprises a heteromeric restriction endonuclease. More preferably the endonuclease comprises R.Bpu10I.

Furthermore, the present invention provides use of a nickase as defined above to introduce one or more site-specific nicks into pre-selected strands of a DNA duplex. In one preferred embodiment the nickases are used in the production of circular single-stranded DNA from circular double-stranded DNA. The circular double-stranded DNA may typically be a supercoiled plasmid. The circular double-stranded DNA should have at least one recognition site for the nickase. If there is more than one nickase recognition site on the circular double-stranded DNA, the sites should be in the same orientation towards each other, so that nicks are introduced into only one strand. The DNA is nicked by incubation in the presence of the nickase to produce a nicked form of the circular double-stranded DNA. Where the DNA is a supercoiled plasmid, the nicked form will typically have a different rate of migration in an agarose gel. Preferably the completeness of the process is then monitored by gel electrophoresis. Nicked DNA may be purified either from the reaction mixture or from an agarose gel by any appropriate technique. The nicked strand may then be degraded with any suitable enzyme possessing 3'–5' or 5'–3' exonuclease activity, but deficient in endonuclease activity, such as *E. coli* exonuclease III or T7 DNA polymerase, typically after changing the reaction buffer. After this procedure circular single-stranded DNA may be purified and can be used for further applications, such as site-specific mutagenesis and DNA sequencing. The strand which has been degraded in the above case may be designated the (+) strand, and thus the (−) strand is produced. If it is desired to produce a single-stranded circular DNA comprising the (+) strand, an analogous procedure may be carried out using a nickase which recognises the same recognition sequence as the above nickase, but cleaves the other strand of the DNA duplex.

An advantage of this method is that in order to obtain single-stranded forms of (+) and (−) strands there is no need to subclone DNA into two different vectors having f1 phage origin or gpII protein recognition sequences in opposite orientations. Typically a pair of nickases recognising the same recognition sequence but capable of cleaving different strands of a DNA duplex may be produced by forming different combinations of native and mutated subunits of a particular heteromeric restriction endonuclease. The principle scheme of this procedure is presented in FIG. 7 by reference to a preferred embodiment involving R.Bpu10I.

In a further aspect the present invention provides a kit for producing one or more site-specific nicks in pre-selected strands of a DNA duplex, comprising a first nickase as defined above and a second nickase as defined above, wherein the first nickase and the second nickase recognise the same recognition sequence, the first nickase is capable of cleaving a first strand of the DNA duplex and the second nickase is capable of cleaving a second strand of the DNA duplex.

In a preferred embodiment of this aspect, the first and second subunits of the first and second nickases comprise subunits from a single heteromeric restriction endonuclease, the first nickase comprises a first subunit capable of cleaving the first strand of the DNA duplex and a second subunit comprising a catalytic domain inactivated to be incapable of cleaving the second strand of the DNA duplex, and the second nickase comprises a first subunit capable of cleaving the second strand of the DNA duplex and a second subunit comprising a catalytic domain inactivated to be incapable of cleaving the first strand of the DNA duplex. The first nickase may be produced by selectively inactivating the catalytic domain of one subunit of a particular heteromeric restriction endonuclease, and the second nickase may be produced by selectively inactivating a different subunit of the particular heteromeric restriction endonuclease. The above kit preferably further comprises an exonuclease, such as *E. coli* exonuclease III, which may be capable of degrading the nicked strand of the DNA duplex. In another embodiment the kit further comprises a circular double-stranded DNA molecule, such as a plasmid, which molecule comprises the recognition sequence recognised by the first and second nickases.

The nickases of the present invention may also be used in the production of nested deletions in a DNA molecule. In this embodiment a nickase according to the present invention may be used to introduce a single-stranded nick into a DNA molecule such as a plasmid. A single strand of the DNA molecule is then partially degraded with a 3'–5' or 5'–3' exonuclease such as E. coli exonuclease III. The extent of this degradation may be controlled by varying the temperature and NaCl concentration. The single stranded stretches may be removed with any suitable nuclease, such as S1 nuclease. The blunt-ended fragments may then be re-ligated to form a circularized plasmid suitable for transformation into competent bacteria. By varying the extent of the exonuclease degradation step, a library of unidirectional deletions is produced which may be used for DNA sequencing. One of the advantages of the present use over the prior art is that a single enzyme (a nickase according to the present invention) is capable of producing an appropriate substrate for exonuclease degradation. The prior art methods rely on the use of two different restriction endonucleases to produce an end with a 3' overhang (resistant to degradation by a 3'–5' endonuclease such as exonuclease III) and an end with a 5' overhang (susceptible to degradation by exonuclease III). Furthermore the present use provides an alternative method of preparing the substrate for exonuclease degradation, which may be used for example when all the other restriction endonucleases which possess recognition sites in the polylinker region of a plasmid containing an insert region to be sequenced also possess recognition sites in the insert region.

The nickases of the present invention may also be used in the preparation of a vector for use in a ligation-independent cloning method. This method allows the ligation step in the construction of recombinant molecules to be omitted, for example in the preparation of a plasmid vector with a DNA insert (28). In the procedures described in the prior art, the DNA fragment to be cloned is incorporated into the vector molecule via complementary homopolymeric nucleotide sequences that are introduced with the help of terminal deoxynucleotidyl transferase (TdT) from calf thymus. Usually polymeric tails approximately 20–30 nt in length of oligo-dG are added to the 3' ends of linearised vector, while complementary oligo-dC tails are added to the fragment to be cloned. Mixing of vector and DNA fragments prepared this way results in the formation of chimeric DNA due to the hybridisation of complementary sequences at the DNA ends. Such DNA effectively transforms competent E. coli cells. Due to the reparative machinery of the cell covalently closed double stranded plasmid DNA is formed inside the cell that can successfully replicate.

This prior art cloning method advantageously avoids the insertion of several different fragments or several copies of the same fragment into a single vector molecule, which often occurs in the procedure involving ligation. An additional advantage is that there is no need to digest the sequence to be cloned with a restriction enzyme in order to obtain specific complementary DNA ends necessary for the ligation procedure. Moreover, before the addition of homopolymeric nucleotide sequences, long DNA molecules can be degraded into smaller fragments by sonication or with non-specific nucleases, e.g. DNase I from bovine pancreas. This way the mixture of DNA fragments to be cloned is statistically totally accidental, in contrast to the DNA fragment mixture obtained after cleavage with any specific restriction enzyme.

However, this method has several disadvantages as well. It was shown that the efficiency of the ligation independent procedure depends greatly on the length of homopolymeric nucleotide tails, namely, the highest efficiency of transformation is achieved when 20 nucleotide length oligo-dG tails are added to the vector (29). If these tails are at least 5 nucleotides shorter or longer the efficiency of transformation with chimerical DNA molecules decreases a multiple of several times. Therefore the vector preparation step for the ligation independent procedure is quite complicated and needs thorough calibration of the addition of homooligonucleotide tails with TdT.

Another known modification of the ligation independent cloning method is used for cloning of PCR fragments so as to avoid a problem related to extra nucleotides at the 3' ends of PCR fragment. Enzymes possessing 3' or 5' exonucleolytic activity can be used for creation of single stranded DNA sequences at the ends of vector and PCR fragment, such as E. coli exodeoxyribonuclease III, T4 or T7 DNA polymerases, Klenow polymerase, lambda phage exodeoxyribonuclease VII, etc. One more enzyme that can be used for above described purpose is uracil DNA glycosylase from E. coli (UDG) that specifically eliminates uridine bases from the DNA strand, thereby labilising the phosphodiester bonds in the DNA backbone (30). It is possible to introduce dU into the 5'-end sequences of PCR fragments during the chemical synthesis of PCR primers. Usage of non-modified dNTPs for PCR procedure results in the synthesis of PCR fragments having uridinylated sequences at their 5' ends and sensitive to UDG. UDG and heat treatment of such PCR products yield the PCR fragments with specific single stranded sequences at the 5' ends.

The most problematic procedure in this case is the preparation of the vector with corresponding single stranded sequences at the ends. Since vector DNA is usually amplified in vivo there is no possibility to introduce dU instead of dT in certain positions. This can be done in two ways: either the vector is amplified by PCR with the primers having uridinylated sequences at their 5' ends or following vector linearisation special adapters with dT substituted for dU in one strand are ligated to the vector molecule. Afterwards the vector is treated with UDG in the same way as the PCR fragment. Therefore vector preparation is both an expensive and a time-consuming procedure.

The ability of the nickases of the present invention to nick specifically pre-selected DNA strand may be applied for efficient preparation of vectors for a ligation independent cloning procedure, as illustrated in FIG. 8 by reference to a preferred embodiment involving R.Bpu10I. Preferably the cloning vector contains a unique restriction site flanked by inverted recognition sequences for the nickase. It is possible to create such a sequence as a cassette that can be ligated into any desired vector and the resulting vector can be amplified in vivo afterwards. According to this embodiment following isolation and purification the vector is linearised with a restriction enzyme cleaving inside the cassette and treated with the appropriate nickase. Thereby nicks are introduced into selected DNA strands and afterwards one DNA strand is degraded with the help of an exonuclease to produce 3' or 5' overhangs of known sequence at the ends of the linearised vector. The insert is preferably prepared by PCR amplification using uridinylated primers with 5' ends complementary to the vector sequence in the overhang regions, and 3' ends complementary to the sequence to be amplified. The insert may then be treated with an enzyme such as E. coli uracil DNA glycosylase to degrade the 5' ends and produce 3' overhangs complementary to the vector sequence. The prepared insert and vector may then be mixed and used to transform competent cells.

In a further aspect the present invention provides a kit for use in a cloning method comprising a nickase as defined above, and a vector comprising a recognition sequence for a restriction endonuclease flanked on each side by the recognition sequence of the nickase, wherein the recognition sequences of the nickase are inverted with respect to each other such that the nickase is capable of cleaving different strands of the vector on each side of the recognition sequence for the restriction endonuclease.

The nickases of the present invention may also be used in the preparation of a covalently closed linear DNA molecule. Such molecules can be used as minimalistic transfection vectors in pharmaceutical applications. For example, the so-called MIDGE (Minimalistic Vectors for Gene Expression in Clinical Applications, 31) are covalently closed DNA transfection vectors used in gene therapy or genetic vaccination. Construction and purification of minimalistic DNA vectors is described and taught in European Patent Applications EP941318A1, EP967274A2. MIDGE minimalistic transfection vectors combine the advantages of viral-vectors (cell-specificity and high expression levels) with those of the plasmid vectors (no immunogenity or danger of virus recombination and relatively low costs). Such vectors contain only the expression cassette (promoter, coding sequence, and terminator/poly-A-site). They are smaller than plasmids by 50–80% and of linear covalently closed topology (31).

According to the prior art methods, MIDGE vectors are made in a three-step process, in which the desired sequence is cut out of a suitable plasmid with at least one restriction endonuclease producing short overhanging ends of single-stranded DNA. Both anti-parallel strands of the DNA-polymer, containing coding sequence, promoter and terminator sequences necessary for its expression, are then ligated with a hairpin-forming, self-complementary deoxyoligonucleotide to generate a double stranded linear molecule closed at both ends. Obtained ligation mixture is afterwards incubated with the second restriction endonuclease that recognizes and cuts a sequence that is absent in generated covalently closed DNA molecule, but is present, at least once, in the remainder of the replicable construct. The restriction digest is subsequently or simultaneously treated with an exonuclease (Exo) that is practically specific for free 3' and 5' ends and the vector backbone is degraded. Remaining MIDGE covalently closed DNA is then subjected to HPLC purification.

For creation of covalently closed linear DNA molecules according to technique described above there is a need to synthesize hairpin-forming, self-complementary deoxyoligonucleotide with ends complementary to desired DNA fragment. The nickases of the present invention can be used to create covalently closed linear DNA molecules without the need for additional oligonucleotide synthesis. Preferably the DNA sequence to be included in the covalently closed linear DNA is first cloned into a plasmid vector containing a pair of recognition sequences for a nickase on each side of the insert sequence, where the recognition sequences of each pair are inverted with respect to each other. In this embodiment the sequence between each pair of recognition sequences comprises a self-complementary sequence capable of forming a hairpin loop, such as an interrupted palindrome. Following treatment with a nickase according to the present invention, the insert region with overhanging ends is excised from the plasmid vector and the self-complementary overhanging ends form closed hairpin loops at either end of the DNA molecule. The resulting structure is preferably ligated to form a covalently closed linear DNA. The covalently closed vector which is also produced may be cleaved with a restriction endonuclease that has no recognition sequences in the insert fragment DNA and then degraded with an enzyme possessing exonuclease activity, for example T7 DNA polymerase. This procedure is illustrated in FIG. 9 with reference to a preferred embodiment using a nickase comprising subunits from R.Bpu10I.

In a further aspect the present invention provides a kit for producing covalently closed linear DNA, comprising a nickase as defined above, and a vector comprising a recognition sequence for a restriction endonuclease flanked on each side by a pair of recognition sequences of the nickase, wherein the recognition sequences of each pair are inverted with respect to each other such that the nickase is capable of cleaving each strand of the vector on each side of the recognition sequence for the restriction endonuclease, and wherein one strand of the sequence between each pair of recognition sequences comprises a self-complementary sequence capable of forming a hairpin loop.

The invention will now be described by way of example only with reference to the following experiments and specific embodiments, and the accompanying drawings, in which:

FIG. 1 shows the amino acid sequence of restriction endonuclease Bpu10I α (SEQ ID NO: 1) and β (SEQ ID NO: 2) subunits.

FIG. 2 shows point mutations in Bpu10I restriction endonuclease α and β subunits and their influence upon the functional activity of subunits.

Figure 8:
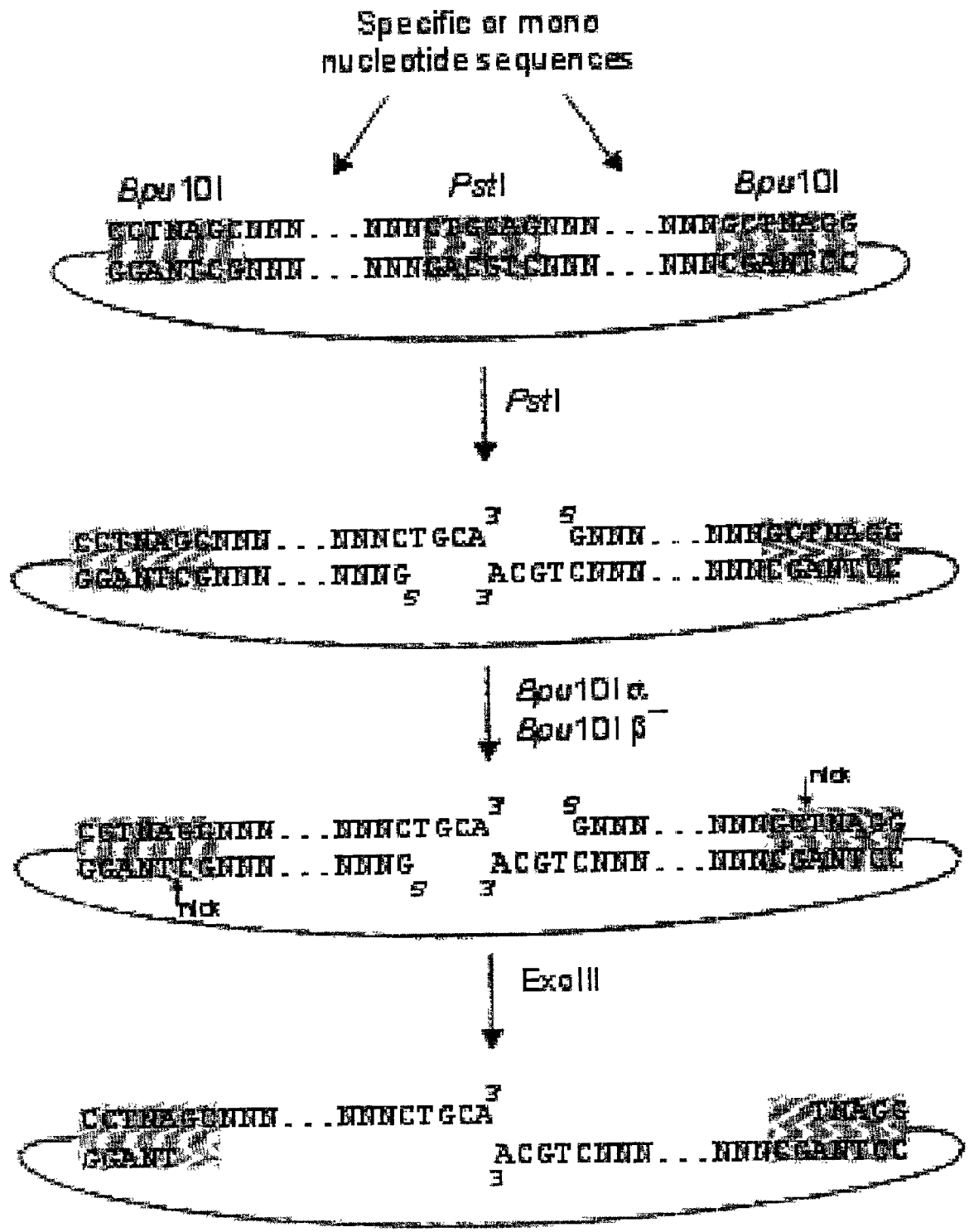

FIG. 8 (SEQ ID NOS: 3–5, respectively, in order of appearance) shows a scheme for vector preparation for ligase independent cloning method using site specific nickases.

Figure 9:
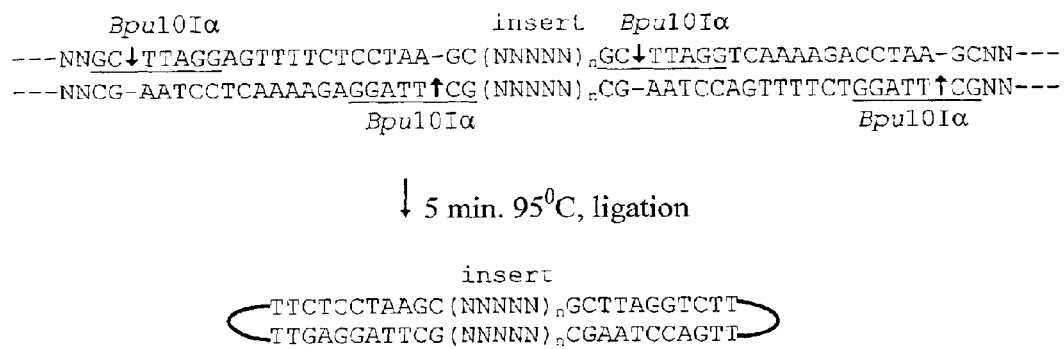

FIG. 9 (SEQ ID NOS: 6–8, respectively, in order of appearance) shows a scheme of preparation of covalently closed DNA molecules using site specific DNA nickases.

Figure 10:
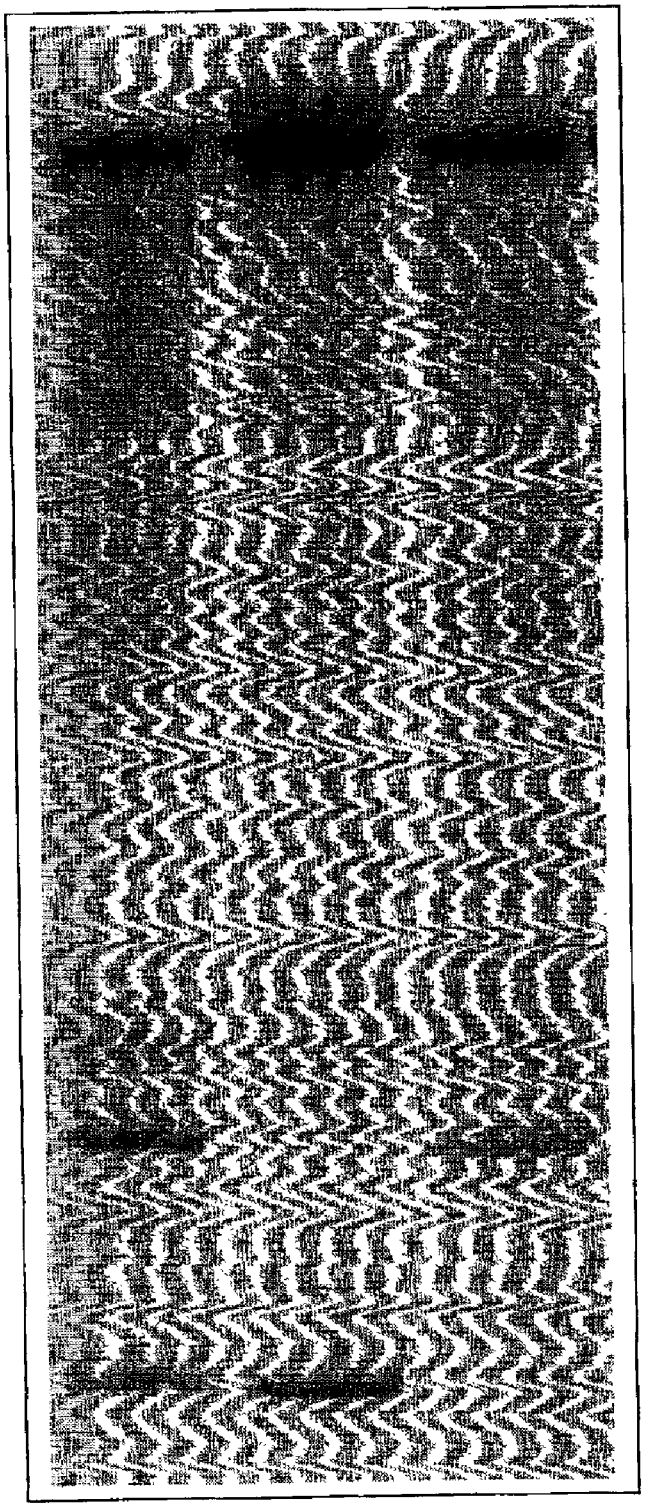

FIG. 10 shows the strand specificity of Bpu10I nickases.

Figure 11:
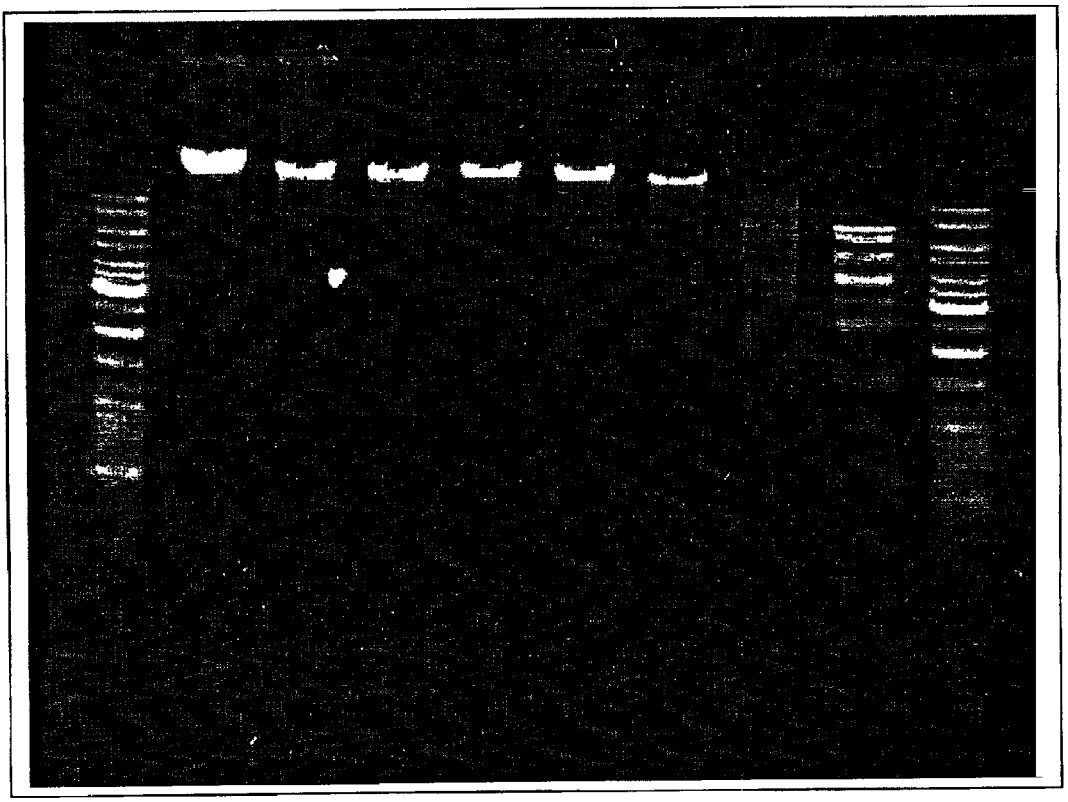

FIG. 11 shows the nicking activity of N.Bpu10Iα (α+βE177A).

EXPERIMENT 1

The Bpu10I restriction-modification system from *Bacillus pumilus* recognizing asymmetric sequence 5'-CCTNAGC-3' comprises four genes: two genes encoding m5C methylases and two genes encoding α and β polypeptides of Bpu10I endonuclease subunits (25, EMBL Acc. No. Y14683, FIG. 1).

For manifestation of R.Bpu 10I enzymatic activity in vivo and in vitro products of both genes bpu10IRα and bpu10IRβ are required. In the presence of only one polypeptide in the reaction mixture neither nicking of DNA nor cleavage of both strands occurs, while after addition of the second polypeptide normal Bpu10I ENase activity is observed. It is proposed that subunits are enzymatically active only when being in heteromeric complex and that probably each subunit nicks different strand of asymmetric DNA sequence.

In order to confirm this proposition point mutations inactivating catalytic activity but retaining protein-protein interaction were introduced into α and β subunits of Bpu10I Enase. For this purpose amino acid sequences of both subunits were analysed trying to identify catalytic centres analogous to those found in other RE, e.g. motif $(E/D)X_{9-15}EXK$ (SEQ ID NO: 9) characteristic for some RE, and the $SD^{171}X_8E^{180}XK^{182}$ (SEQ ID NO: 10) motif in the N-terminal domain of Bpu10I α and $TE^{168}X_8E^{177}XK^{179}$ (SEQ ID NO: 11) motif in the N-terminus of β subunit that corresponded quite well to the consensus one were identified. On the basis of these observations the presumption may be made that $(E/D)X_8EXK$ (SEQ ID NO: 18) motifs might be the catalytic/magnesium binding centres of the proteins described therein. This region was chosen as the target for point mutagenesis and series of mutations were introduced by standard PCR techniques both into α and β subunits (FIG. 1, in which the positions where amino acid substitutions were introduced are underlined.).

Obtained mutant Bpu10I α and β proteins and their combinations with the relevant wild type subunits were analysed for their ability to cleave and nick double stranded DNA. All reactions were performed in the Bpu10I buffer: 10 mM Bis-Tris Propane HCl (pH 6.5), 10 mM $MgCl_2$, 100 mM KCl, 0.1 mg/ml BSA, at 37° C. Point mutations introduced by PCR and their effect on functional activity of α and β subunits are presented in FIG. 2, in which in the column denoted by *, the first letter and number indicate the mutated amino acid and its position, the last letter indicates the amino acid obtained after mutagenesis; +++ indicates activity equal to that of the native enzyme; ++ indicates activity lower than that of the native enzyme; and + indicates only traces of activity are registered.

Figure 3:
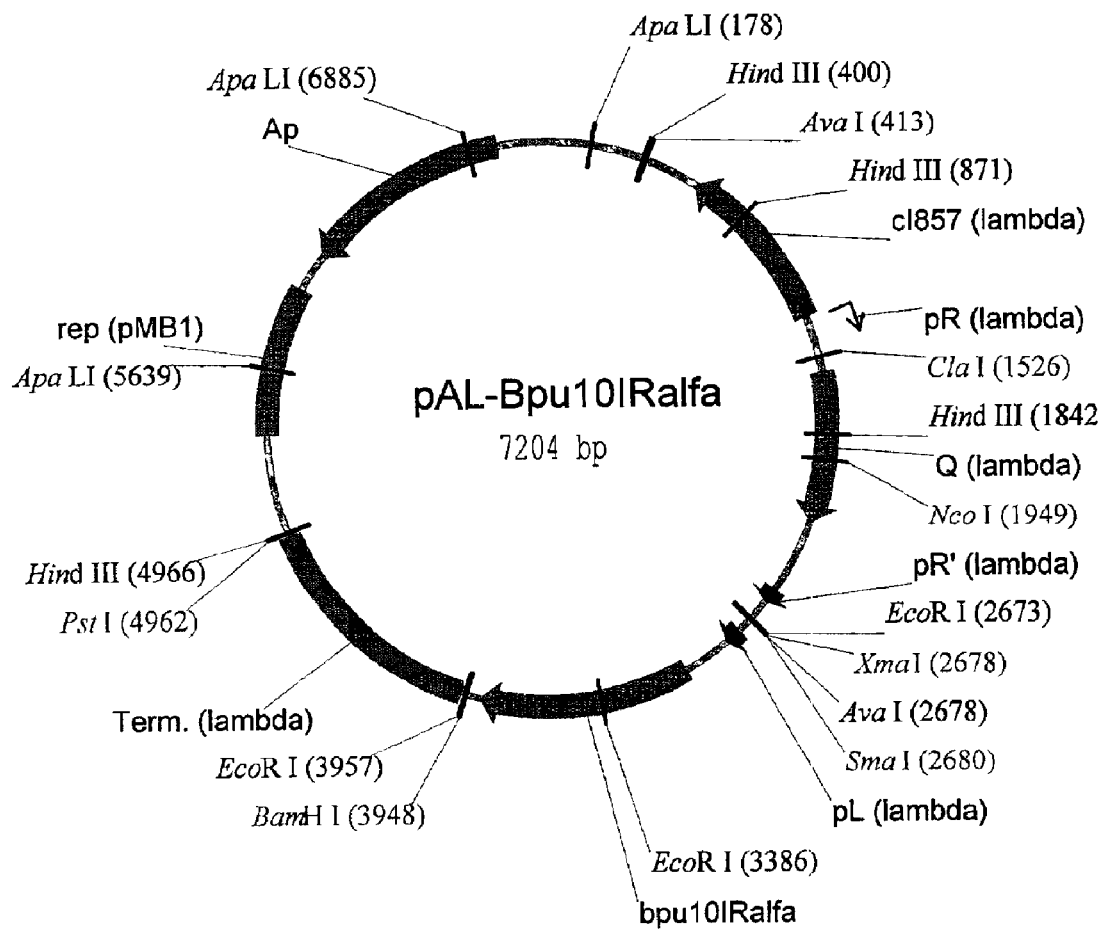
FIG. 3 shows a schematic representation of Bpu10I α protein overexpressing plasmid.
Figure 4:
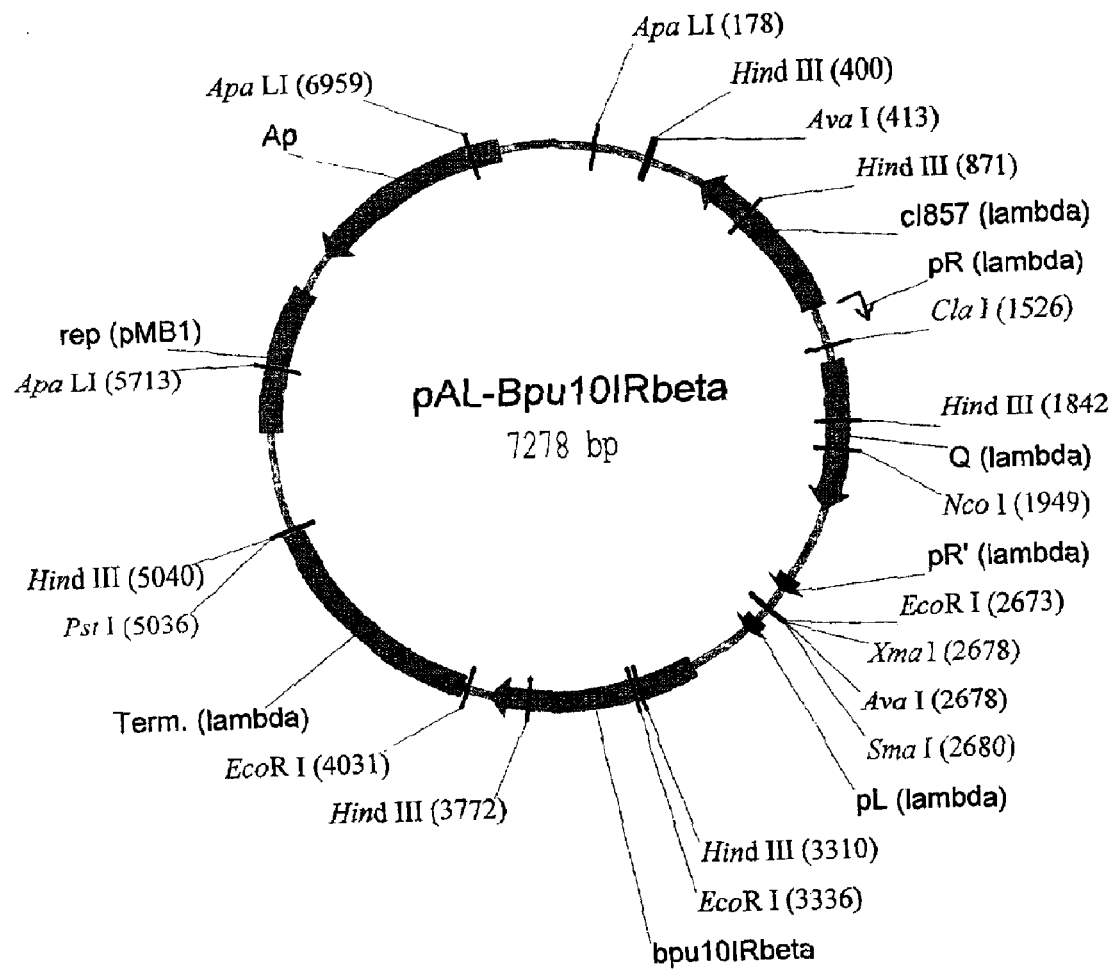
FIG. 4 shows a schematic representation of Bpu10I β protein overexpressing plasmid.
Figure 5:
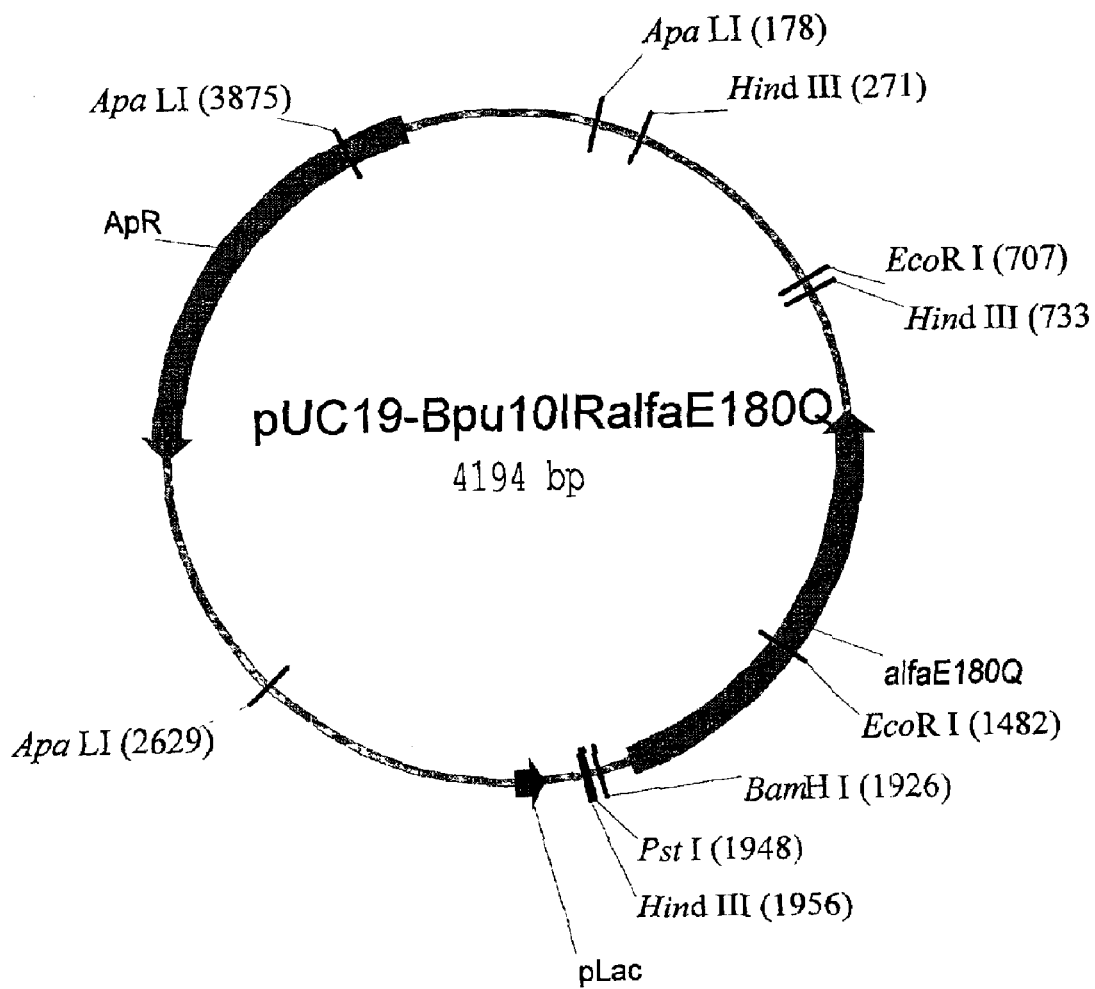
FIG. 5 shows a schematic representation of Bpu10I αE180Q protein overexpressing plasmid.
Figure 6:
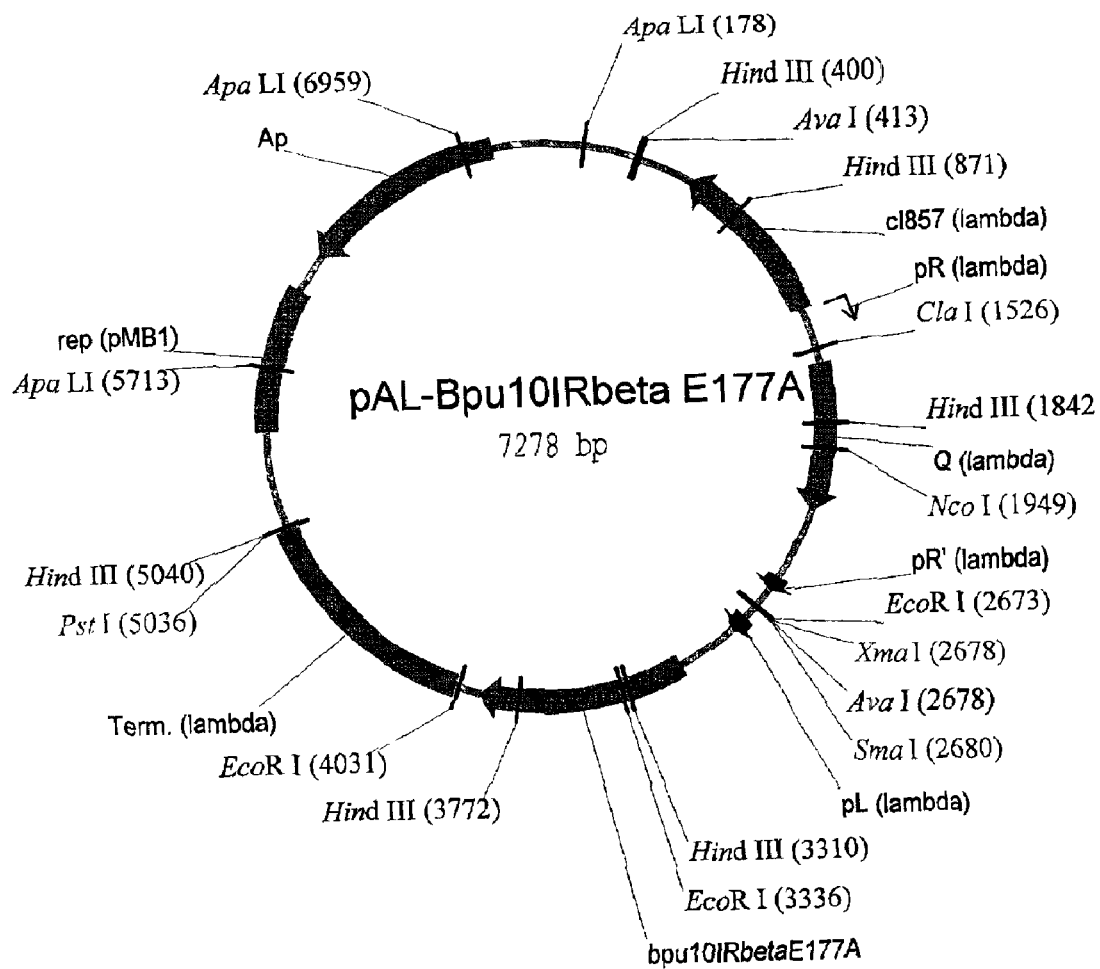
FIG. 6 shows a schematic representation of Bpu10IβE177A protein overexpressing plasmid.
Figure 7:
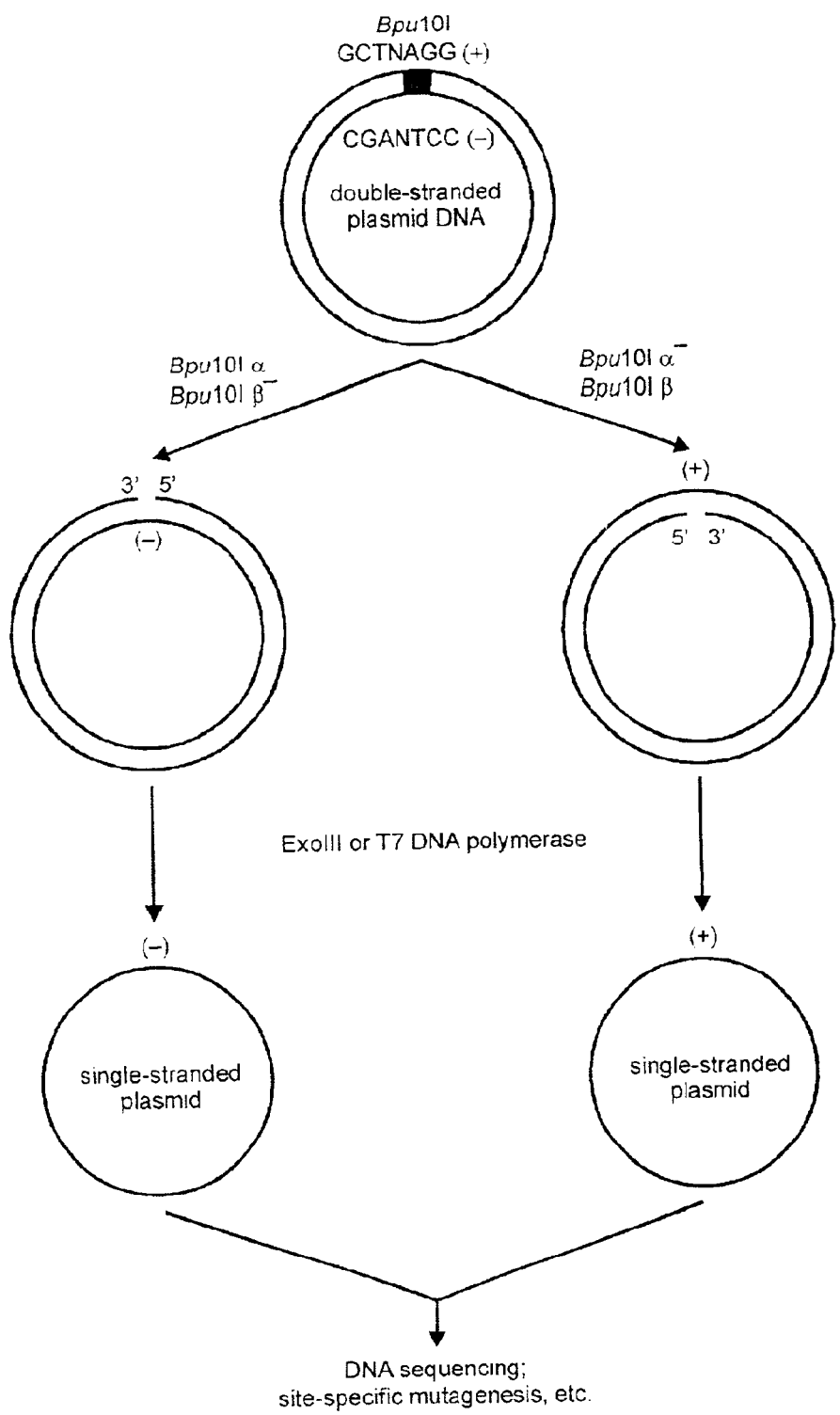
FIG. 7 shows the conversion of double stranded circular plasmid DNA to single stranded form using site specific nickases.

E180Q mutant of α subunit and E177A mutant of β subunit were chosen for further experiments. Proteins were purified to near homogeneity (see Example 1) and it was shown by several different methods (see Example 2, 3) that when E180Q mutant of α subunit (αE180Q) and native β subunit are combined in the reaction mixture the only one strand with the sequence 5'-CC~TNAGC-3' is effectively nicked. Vice versa, the presence of native α subunit and E177A mutant of β subunit (βE177A) in the reaction mixture results in the specific nicking of the opposite DNA strand with the recognition sequence 5'-GC~TNAGG-3' (FIG. 3). The experiment was performed as follows: ΦX174 plasmid DNA, a set of specific primers (#1:5'TGGTTATATTGACCATGC3' (SEQ ID NO: 12), position 1303; #2:5'TTAAAATAGTTGTTATAGATA3' (SEQ ID NO: 13), position 1411), dNTPs and $\alpha[^{33}dATP]$ were used in the extension reaction with T7 DNA polymerase through unique Bpu10I recognition site (position 1361). After inactivation of polymerase by heating at 65° C. for 15 min. labelled extension products were digested in parallel with Bpu10I restriction endonuclease, N.Bpu10Iα (α+βE177A) and N.Bpu10Iβ (αE180Q+β). Digestion reactions were analysed by 10% denaturing PAGE. Due to different distance from the Bpu10I recognition site to the primer annealing sites (60 bp and 46 bp) on the top and bottom DNA strands the cleaved strand could be specifically identified on the gel. In FIG. 10, lane 1 shows labelled ΦX174 DNA digested with Bpu10I restriction endonuclease, lane 2 shows labelled ΦX174 DNA digested with N.Bpu10Iα (α+βE177A), and lane 3 shows labelled ΦX174 DNA digested with N.Bpu10Iβ (αE180Q+β). Primers and fragments cleaved with each nickase are shown below:

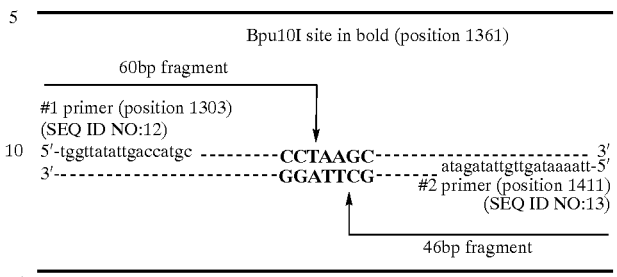

Thereby obtained data confirm the hypothesis that a restriction endonuclease ecognizing a non-palindromic DNA sequence can be converted by site—specific (or on specific) mutagenesis into a specific nickase cleaving only one DNA strand. These data also confirm the presumption that in the native R.Bpu10I enzyme, the a subunit is responsibi for cleavage of DNA strand with the sequence 5'-GC~TNAGC3', while the β subunit—with the sequence 5'-CC~TNAGC-3'.

EXAMPLE 1

Production and Purification of Native and Mutant Subunits of Bpu10I Nickases

Recombinant plasmids for overexpression of Bpu10Iα, Bpu10Iβ, Bpu10IαE180Q and Bpu10IβE177A proteins are presented in FIGS. 3 to 6. The genes for above-referred proteins except for Bpu10IαE180Q were overexpressed by inserting them into expression vector pAL4A (A. Lubys, unpublished, MBI Fermentas) that employs the combination of strong inducible promoter pL and thermo sensitive mutant of repressor protein cI from phage lambda. Gene for Bpu10IαE180Q was overexpressed by inserting it into pUC19 plasmid vector under lac promoter.

A deposit of each of the above plasmids was made under the Budapest Treaty at the Microbial Strain Collection of Latvia (blvd Kronvalda 4, Riga, Latvia, LV-1586). Each deposit was made using E. coli ER2267 transformed as follows:

| Accession Number | Plasmid |
| --- | --- |
| P634 | pUC19-Bpu10I R alfa E180Q |
| P635 | pAL-Bpu 10I R beta E177A |
| P636 | pAL-Bpu 10I R alfa |
| P637 | pAL-Bpu 10I R beta |

Induction scheme for Bpu10Iα, Bpu10Iβ, and Bpu10IβE177A proteins was as follows: E. coli ER2267 cells transformed with relevant overexpressing plasmids (FIGS. 3, 4 and 6) were cultivated overnight in liquid LB medium supplemented with ampicillin (50 mg/l) at 30° C. The overnight culture was added to fresh LB medium supplemented with ampicillin (50mg/l) and propagated at 37° C. to late-log phase ($OD_{600}$ 1.2–1.4). The cells then were harvested by centrifugation.

E. coli RR1 cells with Bpu10IαE180Q overexpressing plasmid (FIG. 5) were cultivated overnight in liquid LB medium supplemented with ampicillin (50 mg/l) at 37° C. The overnight culture was added to fresh LB medium supplemented with ampicillin (50 mg/l) and propagated at 37° C. to late-log phase ($OD_{600}$ 1.2–1.4). RR1 strain is deficient in Lac repressor protein, therefore induction of expression is not necessary. The cells then were harvested by centrifugation. The proteins were purified as follows:

1. Purification of Bpu10Iα: All the following procedures were performed either on ice or at 4° C. Cell biomass was resuspended in Buffer A (10 mM Tris-HCl pH7.0, 1 mM EDTA, 7 mM 2-mercaptoethanol) supplemented with 250 mM KCl at the ratio 4 ml buffer/1 g cell biomass and broken by sonication (22 kHz, 100W) for 5–8 min./100 ml suspension. Nucleic acids were eliminated by addition to sonicated suspension of poliethylenimine to 0.7% final concentration and by centrifugation at 10,000 rpm (Beckman JA10 rotor) for 10 min. Supernatant was collected and dry ammonium sulphate was added while slow mixing to 80% saturation. Proteins were precipitated by centrifugation at 10,000 rpm (Beckman JA10 rotor) for 10 min and collected pellet was dissolved in Buffer A supplemented with 150 mM KCl at the ratio 1–2 ml/1 g pellet. Protein suspension was then dialyzed against 30–50 times higher volume of Buffer A supplemented with 150 mM KCl. Resulting protein extract was then loaded onto a phosphocellulose P11 (Whatman) column equilibrated with Buffer A supplemented with 150 mM KCl at the ratio 2–4 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.6–0.7M KCl and was pooled. Pooled fractions were then dialyzed against 20–30 times higher volume of Buffer A supplemented with 150 mM KCl overnight and loaded onto a Bordo Sepharose (Fermentas) column equilibrated with Buffer A supplemented with 150 mM KCl at the ratio 0.5–0.9 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.35–0.52M KCl and was pooled. Pooled fractions were then dialyzed against 20–50 times higher volume of Buffer A supplemented with 150 mM KCl overnight and loaded onto a Heparin Sepharose (Amersham Pharmacia Biotech) column equilibrated with Buffer A supplemented with 150 mM KCl at the ratio 0.3–0.8 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.43–0.6 M KCl and was pooled. Pooled fractions were then dialyzed against 10–20 times higher volume of Storage Buffer (10 mM Tris-HCl pH7.5, 200 mM KCl, 0.1 mM EDTA, 1 mM DTT, 50% v/v glycerol). Described above purification scheme yielded apparently homogenous protein preparation with the molecular weight of about 35 kDa confirmed by Coomasie blue R-250 stained SDS-PAGE gel electrophoresis. Protein concentration was measured according to Bradford (27) and protein preparation was diluted to the final 100 μM concentration with the Storage Buffer supplemented with 0.2 mg/ml BSA.

2. Purification of Bpu10IαE180Q: All the following procedures were performed either on ice or at 4° C. Cell biomass was resuspended in Buffer A (10 mM Tris-HCl pH7.0, 1 mM EDTA, 7 mM 2-mercaptoethanol) supplemented with 250 mM KCl at the ratio 4 ml buffer/1 g cell biomass and broken by sonication (22kHz, 100W) for 5–8 min/100 ml suspension. Nucleic acids were eliminated by addition to sonicated suspension of poliethylenimine to 0.7% final concentration and by centrifugation at 10,000 rpm (Beckman JA10 rotor) for 10 min. Supernatant was collected and dry ammonium sulphate was added while slow mixing to 80% saturation. Proteins were precipitated by centrifugation at 10,000 rpm (Beckman JA10 rotor) for 10 min and collected pellet was dissolved in Buffer A supplemented with 150 mM KCl at the ratio 1–2 ml/1 g pellet. Protein suspension was then dialyzed against 30–50 times higher volume of Buffer A supplemented with 150 mM KCl. Resulting protein extract was then loaded onto a phosphocellulose P11 (Whatman) column equilibrated with Buffer A supplemented with 150 mM KCl at the ratio 2–4 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.8–0.9M KCl and was pooled. Pooled fractions were then dialyzed against 20–30 times higher volume of Buffer A supplemented with 150 mM KCl overnight and loaded onto a Bordo Sepharose (Fermentas) column equilibrated with Buffer A supplemented with 150 mM KCl at the ratio 0.5–0.9 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.51–0.62M KCl and was pooled. Pooled fractions were then dialyzed against 20–50 times higher volume of Buffer A supplemented with 150 mM KCl overnight and loaded onto a Heparin Sepharose (Amersham Pharmacia Biotech) column equilibrated with Buffer A supplemented with 150 mM KCl at the ratio 0.3–0.8 ml sorbent/1 g cell biomass. The column was washed with two column volumes of Buffer A supplemented with 150 mM KCl and a linear gradient of ten column volumes from 0.15M to 1M of KCl dissolved in Buffer A was applied with the flow speed 10 ml/cm$^2$ per hour. The enzyme eluted at 0.51–0.59M KCl and was pooled. Pooled fractions were then dialyzed against 20–50 times higher volume of Buffer A supplemented with 150 mM KCl overnight and loaded onto a AH-Sepharose (Amersham Pharmacia Biotech) column equilibrated with Buffer A supplemented with 150 mM KCl at the ratio 0.3–0.8 ml sorbent/1 g cell biomass. The column was washed with two column volumes of Buffer A supplemented with 150 mM KCl and a linear gradient of ten column volumes from 0.15 M to 1M of KCl dissolved in Buffer A was applied with the flow speed 10 ml/cm$^2$ per hour. The flow-through fraction was then dialyzed against 10–20 times higher volume of Storage Buffer (10 mM Tris-HCl pH7.5, 200 mM KCl, 0.1 mM EDTA, 1 mM DTT, 50% v/v glycerol). Described above purification scheme yielded apparently homogenous protein preparation with the molecular weight of about 35 kDa confirmed by Coomasie blue R-250 stained SDS-PAGE gel electrophoresis. Protein concentration was measured according to Bradford (27) and protein preparation was diluted to the final 100 μM concentration with the Storage Buffer supplemented with 0.2 mg/ml BSA.

3. Purification of Bpu10Iβ and Bpu10IβE177A: The same purification scheme was applied for purification of native and mutant β proteins. All the following procedures were performed either on ice or at 4° C. Cell biomass was resuspended in Buffer A (10 mM Tris-HCl pH7.0, 1 mM EDTA, 7 mM 2-mercaptoethanol) supplemented with 250 mM KCl at the ratio 4 ml buffer/1 g cell biomass and broken by sonication (22 kHz, 100W) for 5–8 min/100 ml suspension. Nucleic acids were eliminated by addition to sonicated suspension of polyethylenimine to 0.7% final concentration and by centrifugation at 10,000 rpm (Beckman JA10 rotor) for 10 min. Supernatant was collected and dry ammonium sulphate was added while slow mixing to 80% saturation. Proteins were precipitated by centrifugation at 10,000 rpm (Beckman JA10 rotor) for 10 min and collected pellet was dissolved in Buffer A supplemented with 150 mM KCl at the ratio 1–2 ml/1 g pellet. Protein suspension was then dialyzed against 30–50 times higher volume of Buffer A supplemented with 150 mM KCl. Resulting protein extract was then loaded onto a phosphocellulose P11 column (Whatman) equilibrated with Buffer A supplemented with 150 mM KCl at the ratio 2–4 ml sorbent/1g cell biomass. The column was washed with two column volumes of Buffer A supplemented with 150 mM KCl and a linear gradient of ten column volumes from 0.15M to 0.6M of KCl dissolved in Buffer A was applied with the flow speed 10 ml/cm$^2$ per hour. The enzyme eluted at 0.3–0.4M KCl and was pooled. Pooled fractions were then dialyzed against 20–30 times higher volume of Buffer A supplemented with 200 mM KCl overnight and loaded onto a Bordo Sepharose (Fermentas) column equilibrated with Buffer A supplemented with 200 mM KCl at the ratio 0.5–2.0 ml sorbent/1 g cell biomass. The column was washed with two column volumes of Buffer A supplemented with 200 mM KCl and a linear gradient of ten column volumes from 0.2M to 1M of KCl dissolved in Buffer A was applied with the flow speed 10 ml/cm$^2$ per hour. The enzyme eluted at 0.5–0.7M KCl and was pooled. Pooled fractions were then dialyzed against 20–40 times higher volume of Buffer A supplemented with 150 mM KCl overnight and loaded onto a AH-Sepharose (Amersham Pharmacia Biotech) column equilibrated with Buffer A supplemented with 150 mM KCl at the ratio 0.5–2.0 ml sorbent/1 g cell biomass. The column was washed with two column volumes of Buffer A supplemented with 150 mM KCl and a linear gradient of ten column volumes from 0.15M to 0.8M of KCl dissolved in Buffer A was applied with the flow speed 10 ml/cm$^2$ per hour. The enzyme activity eluted at 0.3–0.4M KCl and was pooled. Pooled fractions were then dialyzed against 10–20 times higher volume of Buffer A supplemented with 150 mM KCl overnight and loaded onto a Heparin Sepharose (Amersham Pharmacia Biotech) column equilibrated with Buffer A supplemented with 200 mM KCl at the ratio 0.5–2.0 ml sorbent/1 g protein extract. The column was washed with two column volumes of Buffer A supplemented with 200 mM KCl and a linear gradient of ten column volumes from 0.15M to 0.8M of KCl dissolved in Buffer A was applied with the flow speed 10 ml/cm$^2$ per hour. The enzyme activity eluted at 0.3–0.4M KCl and was pooled. Pooled fractions were then dialyzed against 10–20 times higher volume of Storage Buffer (10 mM Tris-HCl pH7.5, 200 mM KCl, 0.1 mM EDTA, 1 mM DTT, 50% v/v glycerol). Described above purification scheme yielded apparently homogenous protein preparations with the molecular weights of about 34 kDa confirmed by Coomasie blue R-250 stained SDS-PAGE gel electrophoresis. Protein concentrations were measured according to Bradford (27) and protein preparations were diluted to the final 100 μM concentrations with the Storage Buffer supplemented with 0.2 mg/ml BSA.

Bpu10I α nickase with the specificity 5'-GC~TNAGG-3' was obtained by mixing of Bpu10Iα and Bpu10IβE177A proteins at the molar ratio 1:3, while Bpu10I β nickase with the sequence specificity 5'-CC~TNAGC-3' was obtained by mixing of Bpu10Iβ and Bpu10IαE180Q proteins at the molar ratio 1:4. The nicking activity was then evaluated either by monitoring the transition of supercoiled plasmid with one Bpu10I recognition site into the nicked form by agarose gel electrophoresis or by nicking of phage lambda DNA, followed by treatment with S1 nuclease from *Aspergillus oryzae* (Fermentas). Electrophoregrams of nicked lambda DNA yielded no fragmentation in non-denaturing conditions, while the subsequent treatment with S1 nuclease, enzyme specifically cleaving single stranded DNA opposing the nick, yielded digestion pattern typical for Bpu10I restriction endonuclease (FIG. 11). In FIG. 11, each lane shows the following:

Lanes 1 and 10: DNA Molecular weight standards (GeneRuler DNA Ladder Mix, Fermentas)
Lane 2: phage λ DNA
Lane 3: phage λ DNA+Bpu10Iα subunit
Lane 4: phage λ DNA+Bpu10Iα subunit+S1 nuclease
Lane 5: phage λ DNA+Bpu10I βE177A subunit
Lane 6: phage λ DNA+Bpu10I βE177A subunit+S1 nuclease
Lane 7: phage λ DNA+N.Bpu10Iα (α+βE177A)
Lane 8: phage λ DNA+N.Bpu10Iα (α+βE177A)+S1 nuclease
Lane 9: phage λ DNA+Bpu10I Application of Specific DNA Nickases Application possibilities of obtained specific DNA nickases are illustrated by following non-limiting examples.

EXAMPLE 2

Production of Single Stranded Circular DNA Molecules from Supercoiled Double Stranded Plasmids in Vitro and their Application in Molecular Biology Techniques: DNA Sequencing, Site-specific Mutagenesis, Differential Display, etc.

pUC19-Bpu plasmid possessing one Bpu10I recognition site was constructed by ligating 399 bp SspI-DraI φX 174 DNA fragment (1007–1406 nt, GenBank/EMBL Acc. No. V01128, J02482, M103483) with one Bpu10I site 5'-CCTAAGC-3' (1361 nt) into SmaI-HincII digested pUC19. Single stranded nicks into the plasmid DNA were introduced by incubating it with either N.Bpu10Iα (α+βE177A) cleaving 5'-GC~TNAGG-3' or with N.Bpu10Iβ (αE180Q+β) cleaving 5'-CC~TNAGC-3'. Nicking reactions were performed as follows: in 50 μl total reaction volume 5 μg of vector DNA were incubated with nicking enzymes (either α or β) prepared as described in Example 1 in Bpu10I buffer (10 mM Bis-Tris Propane HCl (pH 6.5), 10 mM MgCl$_2$, 100 mM KCl, 0.1 mg/ml BSA) at 37° C. for 3 hours.

Nicking enzyme concentration in the reaction mixture was 2 pmol/μl. Completeness of nicking reaction was confirmed by agarose gel electrophoresis and the reaction was terminated by phenol/chloroform deproteinisation followed by DNA precipitation with ethanol. Nicked DNA was incubated with 100μ of E. coli exonuclease III in ExoIII buffer (Fermentas) until according to agarose gel electrophoresis all DNA was converted into single stranded form. Obtained ssDNA after phenol/chloroform deproteinisation followed by DNA precipitation with ethanol was taken into sequencing reactions with standard M13/pUC sequencing primers. Sequencing reactions were performed with Auto Reader DNA sequencing kit (Fermentas) and run on the standard 8% denaturing PAGE sequencing gel in automated gel sequencing unit (ALF Express™ Amersham Pharmacia Biotech). DNA sequences of good quality were obtained only in case when appropriate primer complementary to the expected non-degraded strand (+ or − depending on the applied nicking enzyme) was used for reaction. Primer complementary to the opposite, degraded strand yielded no reaction products.

EXAMPLE 3

Creation of Nested Deletions using Site-specific Nickases pUC19-Bpu plasmid possessing one Bpu10I recognition site was incubated with either N.Bpu10Iα (α+βE177A) cleaving 5'-GC^TNAGG-3' or with N.Bpu10Iβ (αE180Q+β) cleaving 5'-CC^TNAGC-3'. Nicking reactions were performed in the same way as described in Example 2. Completeness of nicking reaction was confirmed by agarose gel electrophoresis and the reaction was terminated by phenol/chloroform deproteinisation followed by DNA precipitation with ethanol. Nicked DNA was then used as a substrate for creation of nested deletions using ExoIII/S1 Deletion kit (Fermentas). All procedures were performed as recommended by manufacturer. Reaction products after ligation were transformed into E. coli by standard calcium techniques (27). Plasmids isolated from recombinant clones corresponding to different time points of ExoIII degradation were subjected to restriction analysis which revealed that depending on the nicking enzyme used DNA degradation occurred either only upstream or only downstream of Bpu10I recognition sequence.

EXAMPLE 4

Vector Preparadon for Ligation Independent Cloning Method pUC57-PKA2 vector plasnild possessing PstI recognition site flanked by two inverted Bpu10I recognition sites was constructed by ligating the following cassette into PaeI-KpnI digested pUC57 (Fermentas):

```
                    PstI            Bpu10Iα
5'-CCTAAGCTCACTCTCAATGGTCTGCAGAGGTCAGACACGCTTAGGCATG-3'

3'-CATGGGATTCGAGTGAGAGTTACCAGACGTCTCCAGTCTGTGCGAATCC-5'
    Bpu10Iα
```

20 μg of plasmid pUC57-PKA2 were treated with N.Bpu10Iα (α+βE177A) cleaving 5'-GC^TNAGG-3' prepared as described in Example 1 in Bpu10I buffer in 400 μl total reaction volume at 37° C. for 3 hours. Nicking enzyme concentration in the reaction mixture was 2 pmol/μl. After nicking reaction was complete as confirmed by agarose gel electrophoresis 10 units of PstI restriction endonuclease were added into reaction mixture and incubation was prolonged at 37° C. for another 2 hours. The reaction was terminated by phenol/chloroform deproteinisation followed by DNA precipitation with ethanol. Digested vector DNA was then incubated with 500 u of E. coli Exonuclease III in Exo III buffer (Fermentas) at 25° C. for 1 min. Exonuclease degradation should result in the formation of the vector molecule possessing 18 nt and 21 nt single stranded protruding 3' ends.

Following uridinilated primers possessing 5' ends complementary to vector DNA sequence and their 3' ends complementary to phage lambda sequence (EMBL/GenBank Acc. No. J02459, 2761–3678) have been synthesized:

```
Seq #1:    5'-CGUGUCUGACCUGAAAAAATA-3'

Seq #2:    5'-GCUCACUCUCAAUGGTGGCGG-3'
```

After PCR reaction on phage lambda DNA expected 943 bp DNA fragment has been amplified. The fragment was either taken directly into reaction with UDG or gel purified. Obtained PCR fragment (approx. 0.2 μg) was mixed with prepared vector DNA (approx. 0.1 μg) in 1× PCR reaction buffer (10 mM Tris-HCl, pH8.8, 50 mM KCl, 0.8% Nonidet P40) containing no magnesium ions, the mixture was treated with E. coli uracil DNA glycosylase at 37° C. for 30 min., and used subsequently for transformation of E. coli JM109 competent cells. Obtained efficiency of transformation was $7.3 \times 10^4$ CFU/1 μg DNA for unpurified PCR fragment or $8.2 \times 10^4$ CFU/1 μg DNA for gel purified PCR fragment.

Colony PCR analysis was performed on 39 randomly selected transformants using standard pUC/M13 direct and reverse sequencing primers, which revealed that all transformants possessed cloned DNA insert of the expected 943 bp length.

EXAMPLE 5

Preparation of Covalently Closed, Double-Stranded Linear DNA Molecules

A special vector/insert plasmid pUC19-800K8 has been constructed where desired insert DNA fragment was flanked with two inverted Bpu10I recognition sequences on each side (FIG. 8). Spacer sequence between two Bpu10I recognition sites comprises interrupted palindrome, which after nicking reaction should form hairpin self-complementary structure between top and bottom DNA strands. Ligation of resulting structure should yield covalently closed linear insert DNA molecule and covalently closed vector backbone. Vector backbone after subsequent cleavage with restriction endonuclease that has no recognition sequences in the insert fragment DNA becomes susceptible to degradation with enzymes possessing exonucleolytic activity, e.g. T7 DNA polymerase.

20 μg of plasmid pUC19-800K8 were treated with N.Bpu10Iα (α+βE177A) cleaving 5'-GC^TNAGG-3' prepared as described in Example 1 in Bpu10I buffer in 400 μl total reaction volume at 37° C. for 3 hours. Nicking enzyme concentration in the reaction mixture was 2 pmol/μl. After nicking reaction was complete as confirmed by agarose gel electrophoresis pUC19-800K8 was incubated at 95° C. for 5 min. and allowed to slow cool to the room temperature in order to inactivate nicking enzyme and to allow self-complementary hairpin structures to anneal at the DNA ends. Nicks were covalently closed by adding ATP to 0.5 mM concentration, T4 DNA ligase (Fermentas) and ligating at room temperature for one hour. The reaction was terminated by phenol/chloroform deproteinisation followed by DNA precipitation with ethanol. Reaction products afterwards were incubated with NsbI restriction endonuclease that had no recognition sequences in the desired insert fragment DNA, but had recognition site in vector backbone. After completion of digestion reaction as confirmed by agarose gel electrophoresis T7 DNA polymerase was added to the reaction mixture and incubation was prolonged for another 30 min. at 37° C. NsbI digestion generates two blunt ended vector backbone fragments that are susceptible to degradation by T7 DNA polymerase due to it's 3'–5' exonuclease activity, while covalently closed insert DNA is resistant to such degradation. It was shown by agarose gel electrophoresis that the only remaining DNA fragment after reaction is the one that corresponds to covalently closed linear insert DNA (FIG. 9).

REFERENCES

1. Terry, G. J. et al: Mechanism of specific site location and DNA cleavage by EcoRI endonuclease. Gene Amplif. Anal. 5 (1987) 103–118.
2. Erskine, S. G. et al: Rapid-reaction analysis of plasmid DNA cleavage by the EcoRV restriction endonuclease. Biochemistry 36 (1997) 7567–7576.
3. Nardone, G. et al: DNA structural polymorphism modulates the kinetics of superhelical DNA cleavage by BamHI restriction endonuclease. J. Biol. Chem. 265 (1990) 15308–15315.
4. Zebala, J. et al: Characterization of steady state, single-turnover, and binding kinetics of the TaqI restriction endonuclease. J. Biol. Chem. 267 (1992) 8097–8105.
5. Siksnys, V. et al: Catalytic and binding properties of restriction endonuclease Cfr9I. Eur. J. Biochem. 217 (1993) 411–419.
6. Nobbs, T. J. et al: DNA excision by the SfiI restriction endonuclease. J. Mol. Biol. 281 (1998) 419–432.
7. Halford, S. E. et al: The EcoRI restriction endonuclease, covalently closed DNA and ethidium bromide. Biochem. J. 199 (1981) 767–777.
8. Osterlund, M. et al: Ethidium-bromide-inhibited restriction endonucleases cleave one strand of circular DNA. Gene 20 (1982) 121–125.
9. Gruenbaum, Y. et al: Restriction enzyme digestion of hemimethylated DNA. Nucleic Acids Res. 9 (1981) 2509–2515.
10. Potter, B. V. L. et al: Cleavage of phosphorothioate-substituted DNA by restriction endonucleases. J. Biol. Chem. 259 (1984) 14243–14248.
11. Eckstein, F. et al: Cleavage of phosphorothioate-containing oligonucleotides and DNA by restriction endonucleases. Abteil. Chem. 8 (1987) 23–27.
12. Taylor, J. W. et al: The use of phosphorothioate-modified DNA in restriction enzyme reactions to prepare nicked DNA. Nucleic Acids Res. 13 (1985) 8749–8763.
13. Sayers, J. R. et al: Strand specific cleavage of phosphorothioate-containing DNA by reaction with restriction endonucleases in the presence of ethidium bromide. Nucleic Acids Res. 16 (1988) 803–813.
14. Taylor, J. W. et al: The rapid generation of oligonucleotide-directed mutations at high frequency using phosphorothioate-modified DNA. Nucleic Acids Res. 13 (1985) 8765–8785.
15. Nakamaye, K. L. et al: Inhibition of restriction endonuclease NciI cleavage by phosphorotioate groups and its application to oligonucleotide-directed mutagenesis. Nucleic Acids Res. 14 (1986) 9679–9698.
16. Walker, G. T. et al: Isothermal in vitro amplification of DNA by a restriction enzyme/DNA polymerase system. Proc. Natl. Acad. Sci. USA 89 (1992) 392–396.
17. Stahl, F. et al: Introduction of asymmetry in the naturally symmetric restriction endonuclease EcoRV to investigate intersubunit communication in the homodimeric protein. Proc. Natl. Acad. Sci. USA 93 5(1996) 6175–6180.
18. Zhang, Y. et al: Chlorella virus NY-2A encodes at least 12 DNA endonuclease/methyltransferase genes. Virology 240 (1998) 366–375.
19. Xia, Y. et al: A site-specific single strand endonuclease activity induced by NYs-1 virus infection of a Chlorella-like green alga. Nucleic Acid Res. 16 (1988) 9477–9487.
20. Abdurashitov, M. A. et al: N.BstSE-site-specific nuclease from *Bacillus stearothermophilus* SE-589-restriction endonuclease production. Mol. Biol. (Mosk) 30 (1996) 1261–1267.
21. Meyer, T. F. et al: Cleavage site of bacteriophage fd gene II-protein in the origin of viral strand replication. Nature 278 (1979) 365–367.
22. Geider, K. et al: Intermediate stages in enzymatic replication of bacteriophage fd duplex DNA. J. Biol. Chem. 257 (1982) 6488–6493.
23. Quick-Strand TM Site-specific mutagenesis kit, NBL Gene Sciences, Inc. advertisement leaflet.
24. Bonaldo, M. F. et al: Normalization and subtraction: two approaches to facilitate gene discovery. Genome Research 6 (1996) 791–806.
25. Stankevicius, K. et al: Cloning and analysis of the four genes coding for Bpu10I restriction-modification enzymes. Nucleic Acids Res. 26 (1998) 1084–1091.
26. Aggarwal, A. K.: Structure and function of restriction endonucleases. Curr Opin Struct Biol. 5 (1995) 11–19.
27. Ausubel, F. M. et al. (1999) Current Protocols in Molecular Biology, Vol.3, Greene Publishing Associates, Inc., and John Wiley and Sons, NY.
28. Aslanidis, C. et al: Ligation-independent cloning of PCR products (LIC-PCR). Nucleic Acids Res. 18 (1990) 6069–6074.
29. Peacock, S. L. et al: Transformation of *E. coli* using homopolymer-linked plasmid chimeras. Biochim. Biophys. Acta 655 (1981) 243–250.
30. Rashtchian, A. et al: Uracil DNA glycosylase-mediated cloning of PCR-amplified DNA: Application to genomic and cDNA cloning. Anal. Biochem. 206 (1992) 91–97.
31. MOLOGEN Home Page, http://www.mologen.com.

What is claimed is:

1. A strand-specific polynucleotide nickase comprising an endonuclease which comprises a first subunit and a second subunit and which recognises an asymmetric nucleotide recognition sequence, wherein the first subunit comprises a catalytic domain capable of cleaving one strand of a DNA duplex, and the second subunit is incapable of cleaving the other strand of the DNA duplex.

2. A nickase according to claim 1, wherein the second subunit comprises an inactivated endonuclease catalytic domain.

3. A nickase according to claim 1, wherein the catalytic domain is incapable of cleaving one strand of the DNA duplex in the absence of the second subunit.

4. A nickase according to claim 1, wherein the recognition sequence comprises 4 or more nucleotides.

5. A nickase according to claim 1, wherein the catalytic domain is capable of cleaving one strand of the DNA duplex within the recognition sequence.

6. A nickase according to claim 1, wherein the first subunit comprises a subunit from a heteromeric restriction endonuclease.

7. A nickase according to claim 1, wherein the second subunit comprises a subunit from a heteromeric restriction endonuclease modified to render inactive the catalytic domain thereof.

8. A strand-specific polynucleotide nickase comprising a heteromeric restriction endonuclease which comprises a first subunit and a second subunit and which recognises an asymmetric nucleotide recognition sequence, wherein the first subunit comprises a catalytic domain capable of cleaving one strand of a DNA duplex, and the second subunit is modified to render the catalytic domain thereof inactive.

9. A nickase according to claim 8, wherein the heteromeric restriction endonuclease comprises R.Bpu10I.

10. A strand-specific polynucleotide nickase comprising a R.Bpu 10I heteromeric restriction endonuclease which comprises a first subunit and a second subunit and which recognises an asymmetric nucleotide recognition sequence, wherein the first subunit comprises a catalytic domain capable of cleaving one strand of a DNA duplex, and the second subunit is modified to render the catalytic domain thereof inactive.

11. A process for producing a strand-specific polynucleotide nickase, which process comprises inactivating the catalytic activity of one subunit of a restriction endonuclease, wherein the endonuclease comprises a first subunit comprising a catalytic domain capable of cleaving one strand of a DNA duplex and a second subunit comprising a catalytic domain capable of cleaving the other strand of the DNA duplex, and the endonuclease recognises an asymmetric nucleotide recognition sequence.

12. A process according to claim 11, wherein the recognition sequence comprises 4 or more nucleotides.

13. A process according to claim 11, wherein the endonuclease is capable of cleaving at least one strand of the DNA duplex within the recognition sequence.

14. A process according to claim 11, wherein the endonuclease comprises a heteromeric restriction endonuclease.

15. A process according to claim 14, wherein the endonuclease comprises R.Bpu10I.

16. A process according to claim 11, wherein the step of inactivating the catalytic activity of one subunit of the restriction endonuclease comprises non-specific mutagenesis of the subunit.

17. A process according to claim 11, wherein the step of inactivating the catalytic activity of one subunit of the restriction endonuclease comprises identifying the catalytic domain of the subunit and subsequently introducing mutations into the catalytic domain by site-specific mutagenesis.

18. A process according to claim 17, wherein the catalytic domain is identified by comparing the protein sequence of the subunit with the protein sequence motifs from other restriction endonucleases.

19. A strand-specific polynucleotide nickase obtainable by a process as defined in any of claims 11 to 18.

20. A process for producing a strand-specific polynucleotide nickase, which process comprises inactivating the catalytic activity of one subunit of a heteromeric restriction endonuclease, wherein the endonuclease comprises a first subunit comprising a catalytic domain capable of cleaving one strand of a DNA duplex and a second subunit comprising a catalytic domain capable of cleaving the other strand of the DNA duplex, and the endonuclease recognises an asymmetric nucleotide recognition sequence.

21. A process for producing a strand-specific polynucleotide nickase, which process comprises inactivating the catalytic activity of one subunit of a heteromeric restriction endonuclease R.Bpu10I.

22. A method for introducing one or more site-specific nicks into pre-selected strands of a DNA duplex, which comprises contacting the DNA duplex with a nickase as defined in claim 1 under conditions to permit nickase activity.

23. A method according to claim 22, wherein the DNA duplex comprises circular double-stranded DNA, and further comprising removing the nicked strand to produce circular single-stranded DNA.

24. A method according to claim 22, which further comprises production of nested deletions in a DNA molecule.

25. A method according to claim 22 wherein the one or more site-specific nicks produce a vector for use in a ligation-independent cloning method.

26. A method according to claim 22, further comprising producing a covalently closed linear DNA molecule.

27. A kit for producing one or more site-specific nicks in pre-selected strands of a DNA duplex, comprising a first nickase as defined in claim 1 and a second nickase as defined in claim 1, wherein the first nickase and the second nickase recognise the same recognition sequence, the first nickase is capable of cleaving a first strand of the DNA duplex and the second nickase is capable of cleaving a second strand of the DNA duplex.

28. A kit according to claim 27, wherein the first and second subunits of the first and second nickases comprise subunits from a single heteromeric restriction endonuclease, wherein the first nickase comprises a first subunit capable of cleaving the first strand of the DNA duplex and a second subunit comprising a catalytic domain inactivated to be incapable of cleaving the second strand of the DNA duplex, and wherein the second nickase comprises a first subunit capable of cleaving the second strand of the DNA duplex and a second subunit comprising a catalytic domain inactivated to be incapable of cleaving the first strand of the DNA duplex.

29. A kit according to claim 27, for producing circular single-stranded DNA from circular double-stranded DNA, which kit further comprises an exonuclease.

30. A kit according to claim 29, wherein the kit further comprises a circular double-stranded DNA molecule comprising the recognition sequence recognised by the first and second nickases.

31. A kit for use in a cloning method comprising a nickase as defined in claim 1, and a vector comprising a recognition sequence for a restriction endonuclease flanked on each side by the recognition sequence of the nickase, wherein the recognition sequences of the nickase are inverted with respect to each other such that the nickase is capable of cleaving different strands of the vector on each side of the recognition sequence for the restriction endonuclease.

32. A kit for producing covalently closed linear DNA, comprising a nickase as defined in claim 1, and a vector comprising a recognition sequence for a restriction endonuclease flanked on each side by a pair of recognition sequences of the nickase, wherein the recognition sequences of each pair are inverted with respect to each other such that the nickase is capable of cleaving each strand of the vector on each side of the recognition sequence for the restriction endonuclease, and wherein one strand of the sequence between each pair of recognition sequences comprises a self-complementary sequence capable of forming a hairpin loop.

* * * * *